United States Patent [19]
Roy et al.

[11] Patent Number: 6,156,060
[45] Date of Patent: Dec. 5, 2000

[54] STATIC DEVICES AND METHODS TO SHRINK TISSUES FOR INCONTINENCE

[75] Inventors: Loren L. Roy, San Jose; Frank W. Ingle, Palo Alto; George A. Morrison, Foster City; Brian J. Mosel, Dublin, all of Calif.

[73] Assignee: SURx, Inc., Pleasanton, Calif.

[21] Appl. No.: 09/170,767

[22] Filed: Oct. 13, 1998

Related U.S. Application Data

[60] Provisional application No. 60/094,964, Jul. 31, 1998.

[51] Int. Cl.$^7$ .............................. A61B 19/00; A61F 7/12; A61N 1/00
[52] U.S. Cl. ............................ 607/113; 607/116; 607/99; 607/138; 128/898
[58] Field of Search ............................... 607/116, 98, 99, 607/96, 138, 115, 113

[56] References Cited

U.S. PATENT DOCUMENTS

| | | | |
|---|---|---|---|
| 3,934,589 | 1/1976 | Zimmer | 128/303.1 |
| 4,453,536 | 6/1984 | Abild | 128/1 R |
| 4,679,561 | 7/1987 | Doss | 128/422 |
| 4,765,331 | 8/1988 | Petruzzi et al. | 128/303.14 |
| 4,802,479 | 2/1989 | Haber et al. | 128/344 |
| 5,056,531 | 10/1991 | Shimoyama | 128/784 |
| 5,190,517 | 3/1993 | Zieve et al. | 604/72 |
| 5,281,217 | 1/1994 | Edwards et al. | 606/41 |
| 5,293,869 | 3/1994 | Edwards et al. | 128/642 |
| 5,314,465 | 5/1994 | Maurer et al. | 128/788 |
| 5,314,466 | 5/1994 | Stern et al. | 607/156 |
| 5,370,671 | 12/1994 | Maurer et al. | 607/41 |
| 5,370,675 | 12/1994 | Edwards et al. | 607/101 |
| 5,423,811 | 6/1995 | Imran et al. | 606/41 |
| 5,437,664 | 8/1995 | Cohen et al. | 606/42 |
| 5,458,596 | 10/1995 | Lax et al. | 606/31 |
| 5,480,417 | 1/1996 | Hascoet et al. | 607/101 |
| 5,496,312 | 3/1996 | Klicek | 606/34 |
| 5,514,130 | 5/1996 | Baker | 606/41 |
| 5,536,267 | 7/1996 | Edwards et al. | 606/41 |
| 5,556,396 | 9/1996 | Cohen et al. | 606/42 |
| 5,569,242 | 10/1996 | Lax et al. | 606/42 |
| 5,588,960 | 12/1996 | Edwards et al. | 604/20 |
| 5,697,882 | 12/1997 | Eggers et al. | 604/114 |
| 5,697,909 | 12/1997 | Eggers et al. | 604/114 |
| 5,769,880 | 6/1998 | Truckai et al. | 607/101 |
| 5,899,897 | 5/1999 | Rabin et al. | 606/21 |
| 5,957,920 | 9/1999 | Baker | 606/33 |
| 6,035,238 | 3/2000 | Ingle et al. | 607/98 |
| 6,044,846 | 4/2000 | Edwards | 128/898 |

FOREIGN PATENT DOCUMENTS

| | | | |
|---|---|---|---|
| WO 97/20510 | 6/1997 | WIPO | A61B 17/39 |
| WO 98/05380 | 2/1998 | WIPO | A61N 1/40 |

*Primary Examiner*—Linda C. M. Dvorak
*Assistant Examiner*—Jocelyn Debra Ram
*Attorney, Agent, or Firm*—Townsend Townsend & Crew LLP; Mark D. Barrish, ESQ.

[57] ABSTRACT

The invention provides improved devices, methods, and systems for repeatably and reliably contracting fascia and other support tissues, particularly for the treatment of urinary incontinence. Rather than relying on a surgeon's ability to observe, direct, and control the selective shrinking of pelvic support tissues, a relatively large surface of a tissue contraction system is placed statically against the target tissue. Sufficient controlled energy is transmitted from the surface into the engaged tissue to contract the tissue and inhibit incontinence (or otherwise provide the desired therapeutic results).

9 Claims, 16 Drawing Sheets

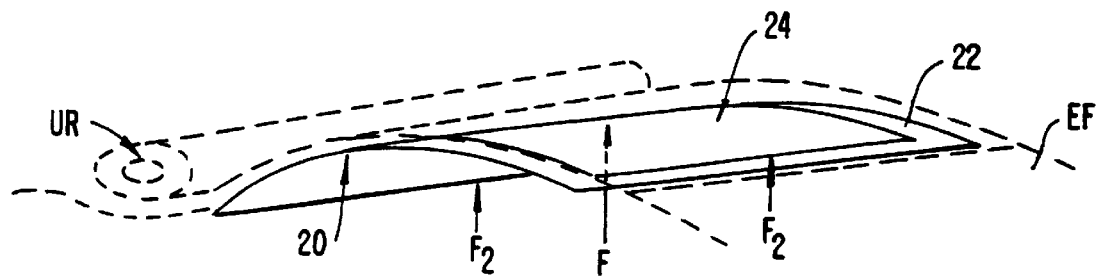
FIG. 15.
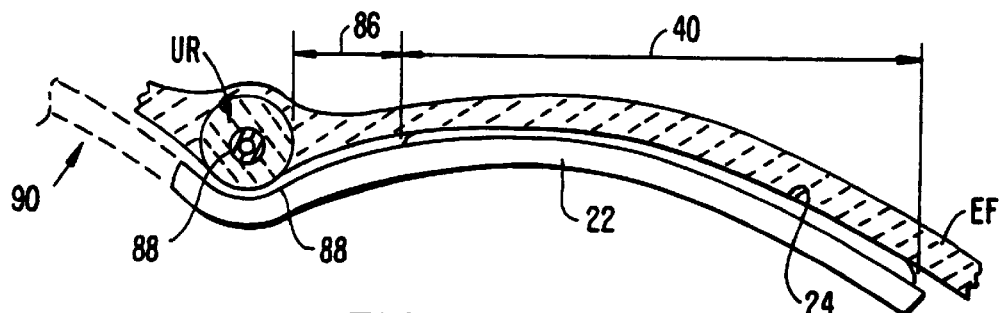
FIG. 16.
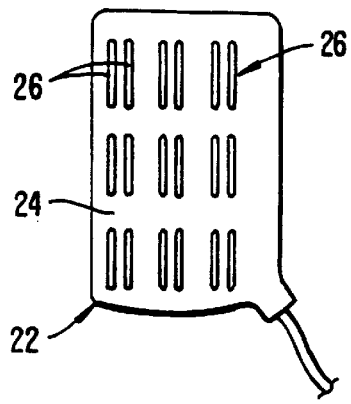     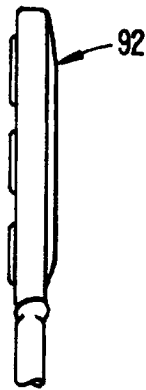     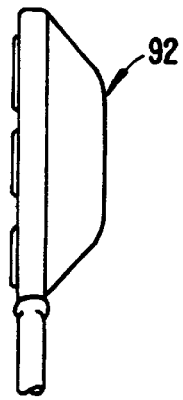
FIG. 17A.    FIG. 17B.    FIG. 17C.

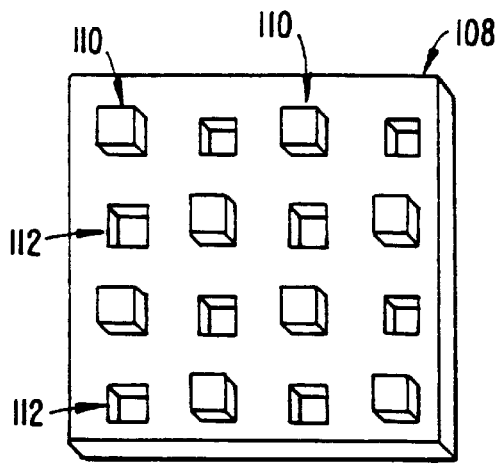
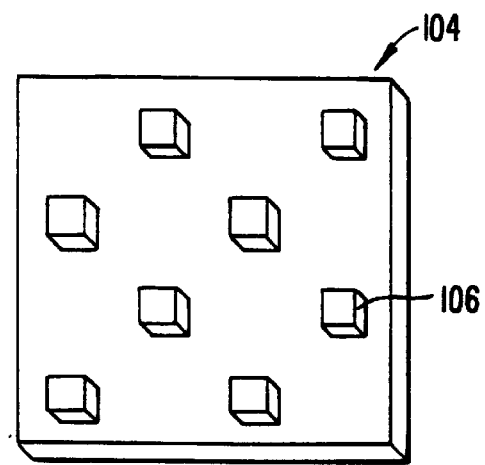
FIG. 19A.   FIG. 19B.
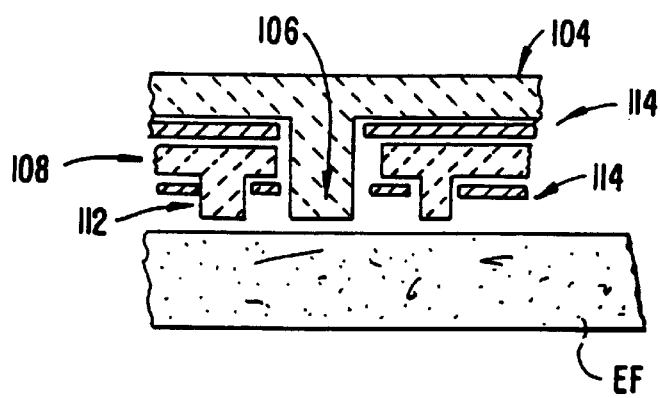
FIG. 19C.
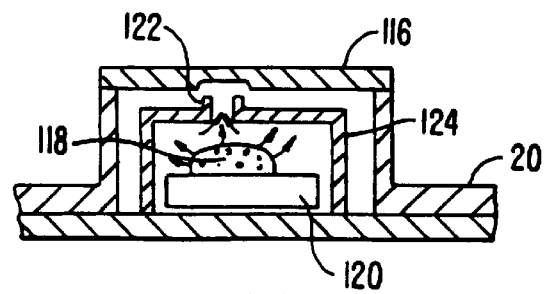
FIG. 20.

STATIC DEVICES AND METHODS TO SHRINK TISSUES FOR INCONTINENCE

This application is a continuation of, and claims the benefit of priority from, Provisional U.S. Patent Application Ser. No. 60/094,964, filed Jul. 31, 1998, the full disclosure of which is incorporated herein by reference.

BACKGROUND OF THE INVENTION

1. Field of the Invention

The present invention generally relates to medical devices, methods and systems for selectively contracting tissues, particularly for the treatment of urinary incontinence.

Urinary incontinence arises in both men and women with varying degrees of severity, and from different causes. In men, the condition most frequently occurs as a result of prostatectomies which result in mechanical damage to the urethral sphincter. In women, the condition typically arises after pregnancy when musculoskeletal damage has occurred as a result of inelastic stretching of the structures which support the genitourinary tract. Specifically, pregnancy can result in inelastic stretching of the pelvic floor, the external sphincter, and the tissue structures which support the bladder and bladder neck region. In each of these cases, urinary leakage typically occurs when a patient's abdominal pressure increases as a result of stress, e.g., coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt a behavior modification intended to reduce the incidence of urinary leakage.

In cases where such non-interventional approaches are inadequate or unacceptable, the patient may undergo surgery to correct the problem. A wide variety of procedures have been developed to correct urinary incontinence in women. Several of these procedures are specifically intended to support the bladder neck region. For example, sutures, straps or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

An alternative surgical procedure which is performed to enhance support of the bladder is the Kelly plication. This involves midline plication of the fascia, particularly for repair of central defects. In this transvaginal procedure, the endopelvic fascia from either side of the urethra is approximated and attached together using silk or linen suture. A similar procedure, anterior colporrhaphy, involves exposing the pubocervical fascia and reapproximating or plicating portions of this tissue from either side of the midline with absorbable sutures. While the Kelly plication and its variations are now often used for repair of cystocele, this procedure was originally described for the treatment of incontinence.

Each of these known procedures has associated shortcomings. Surgical operations which involve midline plications or direct suturing of the tissues of the urethra or bladder neck region require great skill and care to achieve the proper level of artificial support. In other words, it is necessary to occlude or support the tissue sufficiently to inhibit urinary leakage, but not so much that intentional voiding is made difficult or impossible. Balloons and other bulking agents which have been inserted can migrate or be absorbed by the body. The presence of such foreign body inserts can also be a source of urinary tract infections.

Alternative devices, systems, and methods for treatment of urinary incontinence have recently been proposed in U.S. patent application Ser. No. 08/910,370, filed Aug. 13, 1997, and assigned to the assignee of the present invention. This reference, which is incorporated herein by reference, describes techniques for treating urinary incontinence by applying sufficient energy to tissue structures that comprise or support the patient's urethra so as to cause partial shrinkage of the tissue, and thereby inhibit incontinence. Hence, these techniques generally involve selectively contracting a patient's own pelvic support tissues, often applying gentle heating of the collagenated endopelvic structures to cause them to contract without imposing significant injury on the surrounding tissues. U.S. patent application Ser. No. 08/910,775, filed Aug. 13, 1997, describes related non-invasive devices, methods and systems for shrinking of tissues and is also incorporated herein by reference.

While these new methods for treatment of incontinence by selectively contracting tissues represent a significant advancement in the art, still further improvements would be desirable for treating urinary incontinence in men and women. In particular, it would be desirable to provide devices and therapies to reliably and repeatably contract tissues so as to effect the intended physiological change. It would be best if these improved techniques and structures could provide reliable results independent of the normal variations in the skill and experience of the surgeon. It would further be desirable if these improved techniques could be performed using minimally invasive techniques so as to reduce patient trauma, while retaining and/or enhancing the overall efficacy of the procedure.

2. Description of the Background Art

The following U.S. patents and other publications may be relevant to the present invention: U.S. Pat. Nos. 4,453,536; 4,679,561; 4,765,331; 4,802,479; 5,190,517; 5,281,217; 5,293,869; 5,314,465; 5,314,466; 5,370,675; 5,423,811; 5,458,596; 5,496,312; 5,514,130; 5,536,267; 5,569,242; 5,588,960; 5,697,882; 5,697,909; and P.C.T. Published Application No. WO 97/20510.

SUMMARY OF THE INVENTION

The present invention provides improved devices, methods, and systems for repeatably and reliably contracting fascia and other support tissues, particularly for the treatment of urinary incontinence. The techniques of the present invention generally enhance the support provided by the natural tissues of the pelvic floor. Rather than relying entirely on the surgeon's ability to observe, direct, and control the selective shrinking of these tissues, the present invention makes use of tissue contraction systems which are placed statically against the target tissue, and which direct sufficient energy into the tissue so as to inhibit incontinence or the like.

In the preferred embodiment, a thin semi-rigid or rigid credit card shaped device is inserted and urged flat against the endopelvic fascia. An array of electrodes is distributed across a treatment surface of the device, and the treatment surface will often be offset laterally from the urethra to avoid injury to the urinary sphincter or other delicate tissues. The treatment surface will often engage a relatively large area of the endopelvic fascia, and will be held in a static position against this tissue while the electrodes are energized under computer control. The electrodes heat and shrink the engaged endopelvic fascia with minimal collateral damage to the surrounding fascia and tissues, while the device structure and controller will together generally avoid ablation of the engaged endopelvic fascia.

Advantageously, sufficient shrinkage can be provided by the device in the static position so that no additional heating/tissue contraction treatments may be required to the endopelvic fascia on the engaged side of the urethra. Hence, the present invention can take advantage of automated energy delivery circuits and/or selectable contraction probes having treatment surfaces of a variety of selectable sizes and shapes so as to predictably contract the target tissue, rather than relying entirely on a surgeon's skill to contract the proper amount of tissue, for example, by manually "painting" a small electrode along the tissue surface, and may also reduce fouling along the electrode/tissue interface.

In a first aspect, the present invention provides a method for use in a therapy for inhibiting incontinence. The therapy effects a desired contraction of a discrete target region within an endopelvic support tissue. The method comprises engaging a surface of a probe against the target region of the endopelvic support tissue. Energy is directed from an array of transmission elements disposed on the probe surface into the support tissue so as to effect the desired contraction of the target region. The energy directing step is performed without moving the probe.

The energy directing step will often comprise transmitting the energy across a probe surface/tissue interface having a length of at least 10 mm and a width of at least 5 mm. The energy will be sufficient to contract the endopelvic support tissue with minimal damage to underlying tissue. In the exemplary embodiment, the energy directing step comprises applying bipolar electrical energy between a plurality of electrode pairs.

In another aspect, the present invention provides a method for use in a therapy for incontinence. The incontinence therapy includes effecting a desired contraction of an endopelvic fascia. The endopelvic fascia is composed of a left portion and a right portion. The method comprises accessing a first target region along the left or right portion of the endopelvic fascia. The first target region is offset laterally from the urethra. A probe surface is positioned against the first target region, and energy is directed from the positioned probe surface into the first target region so as to effect the desired contraction of the left or right portion of the endopelvic fascia. This energy is directed without moving the positioned probe surface.

Generally, a second target region along the other portion of the endopelvic fascia will also be accessed. The second region is offset laterally from the urethra, so that the urethra is disposed between, and separated from, the first and second target portions. Energy is directed from a probe surface into the second region so as to effect the desired contraction of the other portion without moving the probe surface. These energy directing steps may optionally be performed simultaneously, or may be performed sequentially by moving the probe from one side to the other. A protective zone of the probe surface can be aligned with the urethra to ensure that energy is not inadvertently transmitted from the treatment surface to this delicate tissue structure. Such alignment may be facilitated by introducing a catheter into the urethra.

In another aspect, the invention provides a method for selectively contracting a target tissue. The method comprises aligning a treatment surface of a probe with a first portion of the target tissue. The treatment surface has a peripheral portion and an interior portion. Energy is directed from the treatment surface into the first portion of target tissue so as to contract the first portion. Contraction of the first portion draws a second portion of the target tissue into alignment with the peripheral portion of the treatment surface. Energy can then be selectively directed from the peripheral portion of the treatment surface into the second portion of the target tissue. Advantageously, this allows tissue which was brought into alignment with the probe during the beginning of the treatment to be heated and contracted as it is drawn under the electrodes without over-treatment of the previously contracted tissue.

In another aspect, the invention provides a device for effecting a desired contraction of a discrete target region of a tissue. The target region has a target region size and shape. The device comprises a probe having a treatment surface with a size and shape corresponding to the size and shape of the target region. At least one element is disposed along the treatment surface for transmitting energy from the treatment surface to the target region without moving the probe such that the energy effects the desired contraction.

In another aspect, the invention provides a device for effecting contraction of a target fascial tissue. The target tissue has a fascial surface. The device comprises a probe body having a treatment surface. The treatment surface is oriented for engaging the fascial surface, and has a length of at least about 10 mm and a width of at least about 5 mm. The probe body is at least semi-rigid. An array of electrodes are distributed over the target treatment surface for transmitting energy into the engaged target tissue without moving the probe, such that the energy contracts the target tissue.

In yet another aspect, the invention provides a device for contracting a target tissue having a tissue surface. The device comprises a probe having a treatment surface oriented for engaging the tissue surface of the target tissue. An electrode is disposed on the treatment surface of the probe, and is engageable against the target tissue surface so as to contract the engaged target tissue from an initial size to a contracted size. The electrode comprises a peripheral portion and an interior portion. The interior portion has an area corresponding to the contracted size of the tissue. The peripheral portion is energizeable independently from the interior portion. This advantageous structure allows the tissue immediately surrounding the contracted tissue to be heated and contracted without overtreating (and imposing unnecessary trauma) on the previously contracted tissue.

BRIEF DESCRIPTION OF THE DRAWINGS

FIG. 15 illustrates a semi-rigid probe body which flexes to help ensure the treatment surface of the probe is in contact with the target tissue.

FIG. 16 illustrates a probe having a cavity that receives the urethra to help ensure that the treatment surface is separated from the urethra by a protection zone.

FIGS. 17A–C illustrate front and side views of a probe having a balloon which urges the treatment surface of the probe against the target tissue.

FIGS. 19A–C illustrate a probe having interspersed hot and cold posts.

FIG. 20 is a cross-sectional view showing a probe having a heating element with a limited quantity of a reaction material such that the total heat energy that will be transmitted to the target tissue is limited.

DESCRIPTION OF THE PREFERRED EMBODIMENT

The present invention generally provides methods, devices, and systems which repeatably contract tissue, particularly as a therapy for incontinence. The techniques of the invention will generally involve positioning a probe so that a surface of the probe engages a target tissue statically, that is, without relative movement between the probe and the engaged tissue surface during treatment. Energy will then be transmitted from the treatment surface of the probe into the target tissue so as to effect the desired contraction. This allows the contraction to be controlled by the configuration and/or software of the system, rather than relying on a surgeon's experience to allow him or her to "paint" a small area electrode surface across a sufficient portion of the target region at a proper rate to effect contraction without imposing excessive injury on the target tissue. As these techniques will be effective for controllably and repeatably contracting a wide variety of fascia and other collagenated tissues throughout the body, they will find applications in a wide variety of therapies, including skin wrinkle shrinkage, tightening stretched tendons and ligaments in knees, ankles, and wrists, treatment of droopy eyelids, shrinking large earlobes, and the like. However, the most immediate application for the invention will be to enhance the patient's own natural support of the bladder, bladder neck region, and urethra so as to inhibit urinary incontinence.

The techniques of the present invention will often be used to contract fascia, tendons, and other collagenous tissues, preferably without ablation of these collagenous tissues. As used herein, this means that collagenous tissues are not removed and their function (particularly their structural support function) is not destroyed. Histologically, some tissue necrosis may occur, and the structural strength of the contracted tissue may initially decrease after treatment. Nonetheless, the treated tissues will generally continue to provide at least some structural support, and their structural strength should increase during the healing process so that the healed, contracted tissue has at least almost the same structural strength as, and preferably greater structural strength (for example, stretching less under tension) than before treatment. Collagenous tissues may occasionally be referred to herein as collagenated tissues.

Figure 1:
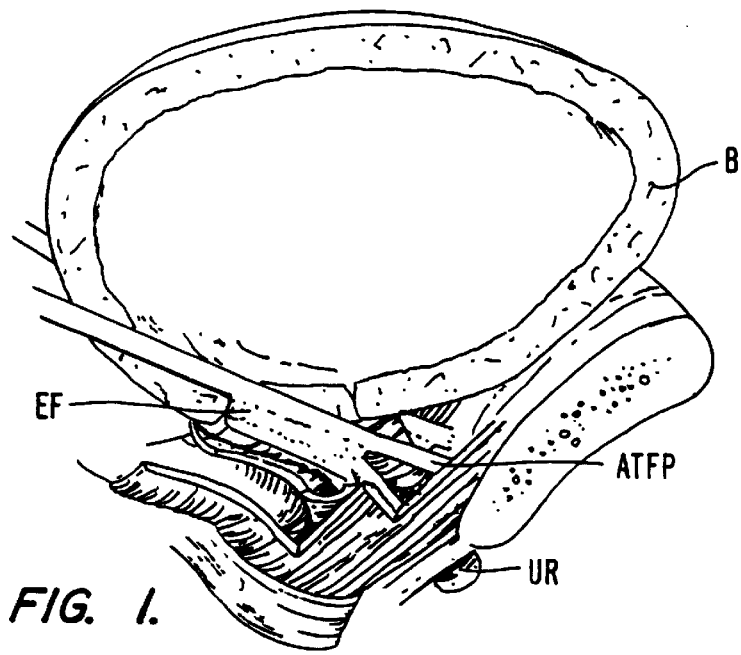
FIG. 1 is a lateral cross-sectional view showing the urinary bladder and a bladder support structure.

The pelvic support tissues which generally maintain the position of much of the genitourinary tract, and particularly the position of urinary bladder B, are illustrated in FIG. 1. Of particular importance for the method of the present invention, endopelvic fascia EF defines a hammock-like structure which extends laterally between the left and right arcus tendinous fascia pelvis ATFP. These later structures extend substantially between the anterior and posterior portions of the pelvis, so that the endopelvic fascia EF largely defines the pelvic floor.

The fascial tissue of the pelvic floor may comprise tissues referred to under different names by surgeons of different disciplines, and possibly even by different practitioners within a specialty. In fact, some surgeons may assign the collagenous support structure referred to herein as the endopelvic fascia one name when viewed from a superior approach, and a different name when viewed from an inferior approach. Some or all of this support structure may comprise two collagenous layers with a thin muscular layer therebetween, or may comprise a single collagenous layer. In general terms, the therapy of the present invention may be directed toward any of the collagenous portions of the support structures for the urethra, bladder neck, and bladder. Hence, the treated tissues may include and/or be referred to as endopelvic fascia, arcus tendinous fascia pelvis, urethropelvic ligaments, periurethral fascia, levator fascia, vesicopelvic fascia, transversalis fascia, and/or vesicle fascia, as well as other collagenous support structures.

In women with urinary stress incontinence due to bladder neck hypermobility, the bladder has typically dropped between about 1.0 cm and 1.5 cm (or more) below its nominal position. This condition is typically due to weakening and/or stretching of the pelvic support tissues, including the endopelvic fascia, the arcus tendinous fascia pelvis, and the surrounding ligaments and muscles, often as a result of bearing children.

When a woman with urinary stress incontinence sneezes, coughs, laughs, or exercises, the abdominal pressure often increases momentarily. Such pressure pulses force the bladder to descend still farther, shortening or misaligning the urethra UR and momentarily opening the urinary sphincter.

Figure 2:
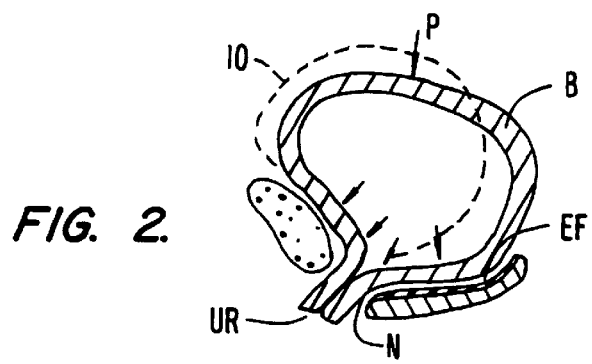
FIG. 2 is a cross-sectional view of a patient suffering from urinary stress incontinence due to inelastic stretching of the endopelvic fascia.
Figure 3:
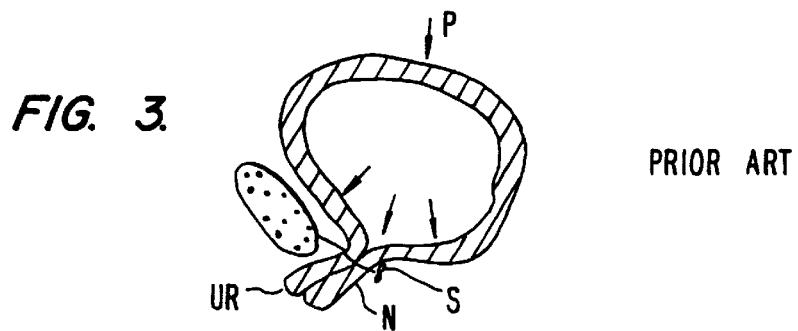
FIG. 3 shows a known method for treating urinary incontinence by affixing sutures around the bladder neck.
Figure 4:
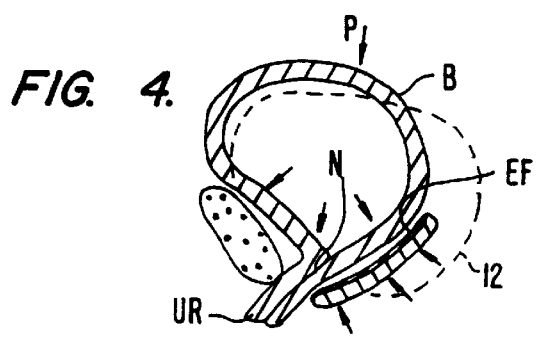
FIG. 4 illustrates improved bladder support provided by contracting the endopelvic fascia according to the principles of the present invention.

As can be most clearly understood with reference to FIGS. 2–4, the present invention generally provides a therapy which effectively reduces the length of the pelvic support tissues and returns bladder B towards its nominal position. Advantageously, the bladder is still supported by the fascia, muscles, ligaments, and tendons of the natural pelvic support tissues.

Referring now to FIG. 2, bladder B can be seen to have dropped from its nominal position (shown in phantom by outline 10). While endopelvic fascia EF still supports bladder B to maintain continence when the patient is at rest, a momentary pressure pulse P opens the bladder neck N resulting in a release of urine through urethra UR.

A known treatment for urinary stress incontinence relies on suture S to hold bladder neck N closed so as to prevent inadvertent voiding, as seen in FIG. 3. Suture S may be attached to bone anchors affixed to the pubic bone, ligaments higher in the pelvic region, or the like. In any case, loose sutures provide insufficient support of bladder neck N and fail to overcome urinary stress incontinence. Over tightening suture S may make normal urination difficult and/or impossible.

As shown in FIG. 4, by reducing the effective length of the natural pelvic support tissues, bladder B may be elevated from its lowered position (shown by lowered outline 12). Alternatively, contraction of selected tissues may reduce or eliminate slack in the support structures without raising the bladder, and/or may reduce the elongation of the support structures to reduce dropping of the bladder when under stress. A pressure pulse P will then be resisted in part by endopelvic fascia EF which supports the lower portion of the bladder, helping maintain the bladder neck in a closed configuration.

Fine tuning of the support provided by the endopelvic fascia is possible through selective modification of the anterior portion of the endopelvic fascia. To close the bladder neck and raise bladder B upward, for example, it may be possible to effect a greater total tissue contraction towards the front. Alternatively, repositioning of bladder B to a more forward position may be affected by selectively contracting the dorsal portion of the endopelvic fascia EF to a greater extent then the forward portion. Hence, the therapy of the present invention may be tailored to the particular weakening exhibited by a patient's pelvic support structures. Regardless, the portion of the endopelvic fascia EF adjacent the bladder neck and urethra UR can remain free of sutures or other artificial support structures which might directly compress the urethra.

Figure 5:
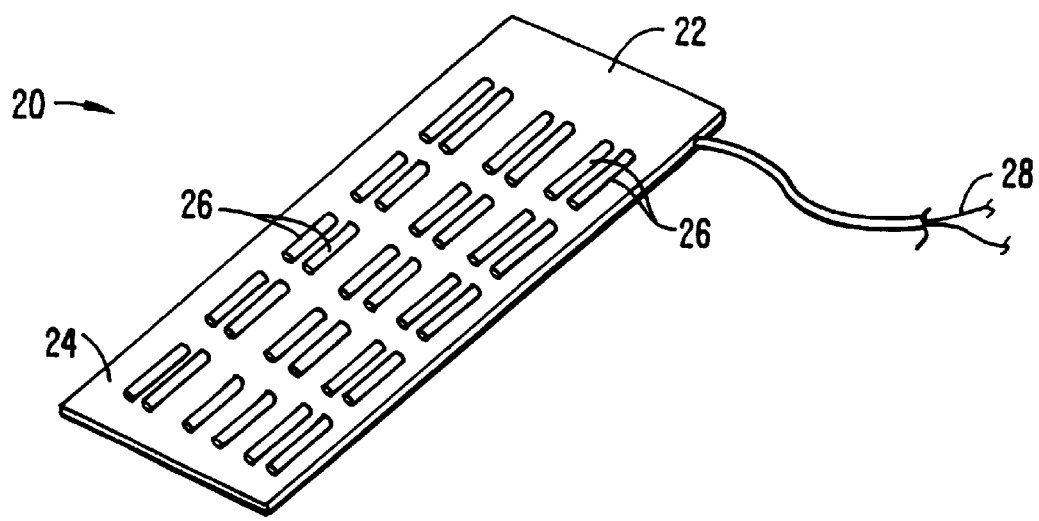
FIG. 5 is a perspective view of a probe having a thin flat credit card shaped body and a treatment surface with a two-dimensional array of bi-polar electrode pairs.

Referring now to FIG. 5, a credit card shaped probe 20 includes a thin flat probe body 22 having a treatment surface 24. A two-dimensional array of electrodes 26 is distributed across treatment surface 24, the electrodes here being arranged in bipolar pairs. Conductors 28, here in the form of a plurality of insulated wires jacketed in a single bundle, extend from probe body 22 for coupling an electrical energy source to electrodes 26.

Figure 5A:
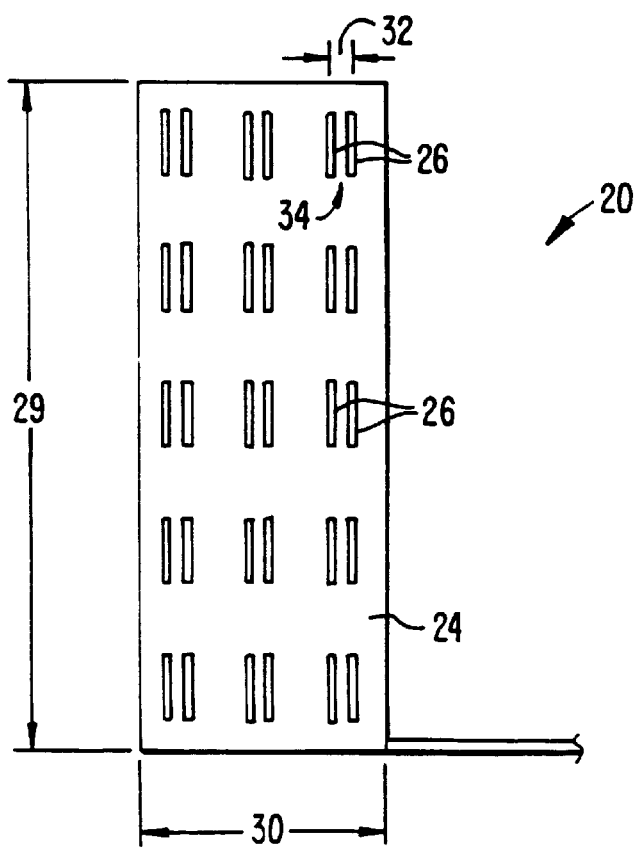
FIG. 5A is a front view of the probe of FIG. 5.

As seen most clearly in FIG. 5A, treatment surface 24 of probe 20 has a length 29 and a width 30 that are significantly greater than a thickness of probe body 22. Length 24 will typically be at least about 10 mm, while width 30 will generally be at least about 5 mm. Preferably, length 28 will be between about 10 and 50 mm, with width 30 being between about 5 and 30 mm.

Probe body 22 will usually have a thickness of between about 1 and 15 mm. In many embodiments, the thickness of probe body 22 will be about 8 mm or less, typically being from about 8 mm to about 1 mm, and preferably being about 5 mm or less. The probe body will often be at least semi-rigid. In other words, although probe body 22 may flex, the probe body will generally have a stiffness greater than that of fascial tissue. This helps ensure that each of electrodes 26 can be effectively coupled to the fascial tissue surface by urging an interior portion of the probe body against the target tissue. Body 22 may flex slightly during such pressure so that both surfaces conform somewhat to each other. Body 22 may be substantially rigid so that the fascial surface conforms substantially entirely to the shape of probe 20. The probe body may comprise a polymer such as polycarbonate, ABS plastic, or the like.

Where electrodes are used to heat the target tissue, the tissue temperature can be controlled in a variety of ways so as to limit variability in efficacy. Feedback to a computer which controls power to electrodes 26 might directly indicate temperature, or the computer might instead control the treatment time. Signals might be provided to the computer indicating the electrical power being used, the electrical energy which has been input to the tissue, or the impedance of the tissue as measured by the current and voltage of the RF energy delivered to the probe. Additionally, the spacing between treated and non-treated regions may be set by the structure of the probe and array, and/or by selectively energizing the electrodes of the probe. This further controls the therapy to eliminate or reduce user variability.

Electrodes 26 may be substantially flush with tissue treatment surface 24, or may alternatively protrude from the tissue treatment surface. When protruding electrodes are used, they will often present a rounded surface for engagement against the fascial tissue so as to minimize the concentration of electrical current density (as might otherwise occur at sharp corners). As is explained in more detail in U.S. patent application Ser. No. 08/910,370, filed Aug. 13, 1997, the full disclosure of which is incorporated herein by reference, the depth of tissue treatment may be varied when using bi-polar electrodes by setting the spacing 32 between a pair of electrodes 34, and/or by setting a diameter or radius of curvature of electrodes 26 where they engage the tissue surface. In the exemplary embodiment, the electrodes have a radius of curvature of 0.012 inches, are formed of stainless steel, and are separated by about six times the radius of curvature (between their inner edges) to limit heating depth to less than about 3 mm. The spacing between electrode pairs should allow treatment of a relatively large amount of fascia without damage to the urethra. Spacing between pairs may also leave some untreated tissue interspersed between the treated regions, which will promote healing. The interspersed untreated areas of the target tissue may comprise fascia and/or other collagenous tissues, and the pairs may be separated such that at least a portion of the untreated tissue can remain at or below a maximum safe tissue temperature throughout treatment, optionally remaining below 60° C., and in some embodiments remaining below 45° C.

Using a bipolar credit card shaped configuration, a fascial tissue can be safely heated to a contraction temperature by transmitting a current between a pair of electrodes having a radius of curvature at the tissue interface in a range from about 0.05 to about 2.0 mm, ideally being about 0.3 mm, where the electrodes are separated by a distance in the range from about 1 to about 10 times the radius of curvature of the electrodes. This generally allows heating of the fascial tissue to a depth in the range between about 0.5 and 10 mm from the engaged tissue surface, typically using an alternating current at a frequency at between about 100 kHz and 10 MHz with a voltage in a range of from about 10 to about 100 volts rms (ideally being about 60 volts rms) and a current in a range from about 0.1 to about 10 rms amps. The driving energy may be applied using an intermittent duty cycle to effect the desired increase in temperature. Generally, the tissue will be heated to a safe contraction temperature in a range from about 70° C. to about 140° C. for a time in the range from about 0.5 to about 40 secs, typically for a time from about 0.5 to about 10 secs.

Figures 5B, 5C:
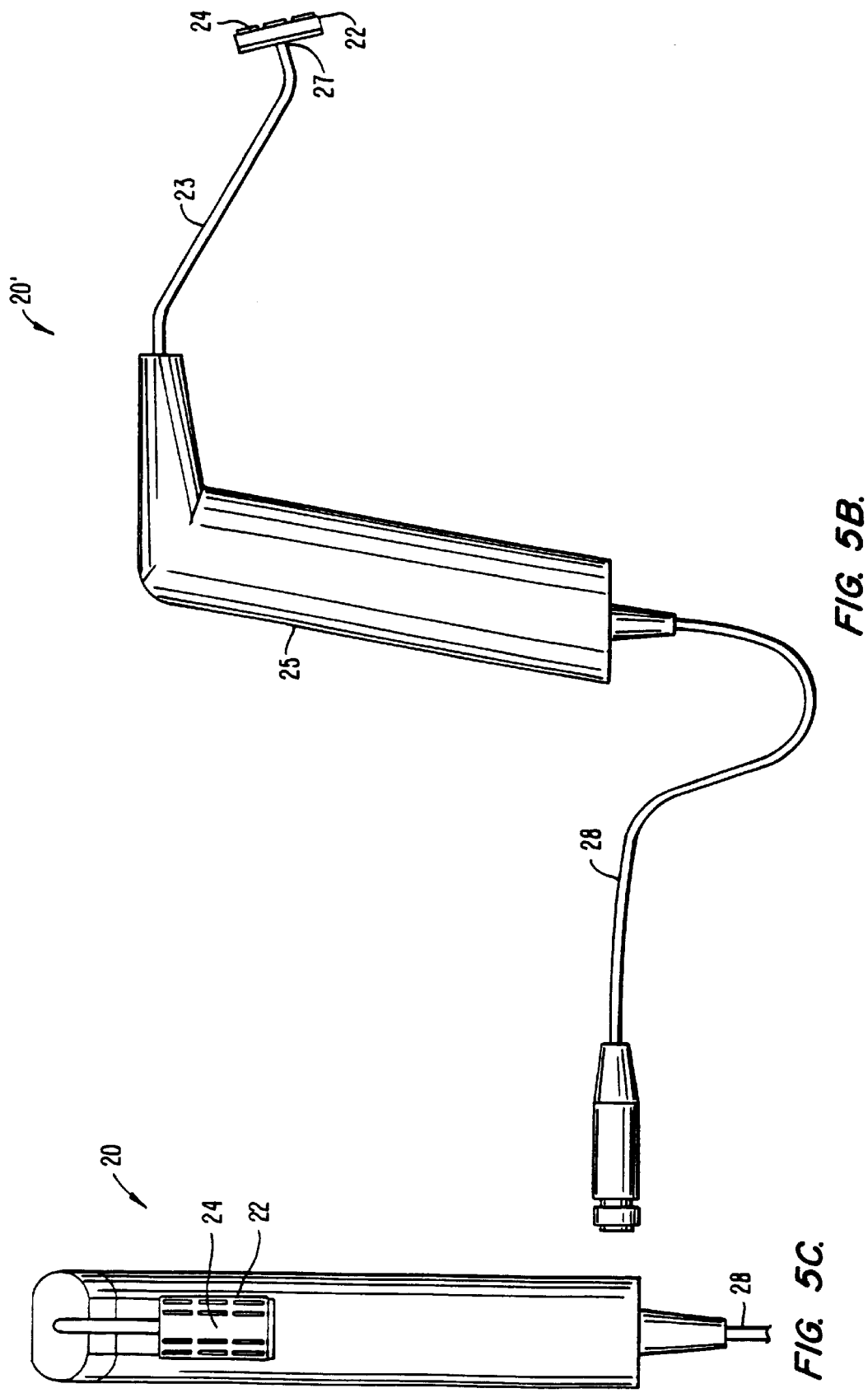
FIGS. 5B and C are side and front views, respectively, of a probe having an electrode array supported by a shaft.

An alternative probe structure 20' is illustrated in FIGS. 5B and C. In this embodiment, probe body 22 is supported by a rigid shaft 23 extending from a handle 25. Shaft 23 may be bent to orient treatment surface 24 to engage the endopelvic fascia. Optionally, a flex joint 27 may be provided at the junction of shaft 23 and probe body 22 to help ensure that the entire treatment surface 24 engages the fascial surface when the treatment surface is held in position manually from handle 25. Joint 27 may comprise a pliable or resilient structure and/or material adjacent the shaft/body interface, such as an elastomer, a polymer, a ball and socket arrangement, a pair of orthogonal pivots, or the like. Shaft 23 may comprise a stainless steel hypotube containing the conductors coupled to electrodes 26, or any of a variety of alternative metal, polymer, or composite structures. The handle will often comprise a polymer such as polycarbonate, ABS plastic, or the like, and may optionally include controls for energizing the electrodes.

The configuration of the electrode array is generally fixed by the probe body structure. This often sets the tissue heating pattern (based on the electrode size and spacing between electrode pairs), as the probe body will be held at a fixed position against the tissue during tissue heating. This predetermined heating pattern helps avoid over-treatment of some tissues and under contraction of others, as can occur when manually painting a small treatment surface repeatedly across the target tissue.

It has been demonstrated that the shape and layout of the electrodes can provide preferential contraction of the target tissue along a desired orientation. Using the elongate electrodes 26 arranged in two series of three end-to-end pairs, and heating each pair of first one series, and then the other series, sequentially (starting with the middle pair), the engaged tissue can be contracted to a significantly greater extent in width (across the electrode pairs) than in length (along the electrodes). In fact, any pattern of elongate heated tissue zones (such as between an elongate pair of electrodes) may provide preferential contraction across the elongate heat zones as compared to along their length, particularly when such elongate heat zones are alternated with elongate untreated zones (such as between the pairs). This can be extremely useful when a surgeon wants to, for example, decrease a lateral width of the endopelvic fascia while minimizing the reduction in its anterior/posterior length.

Probe body 22 will often be formed as a multilayer structure to facilitate electrically coupling conductors 28 to electrodes 26. As shown in FIG. 5, for monopolar operation, only a single conductor need be electrically coupled to the electrodes, while a separate conductor can be coupled to a large return electrode placed on the leg or back of the patient. Bipolar operation will generally include at least two-conductors, while both monopolar and bipolar probes will often include larger numbers of conductors to selectively vary the electrical power across treatment surface 24.

Figure 5D:
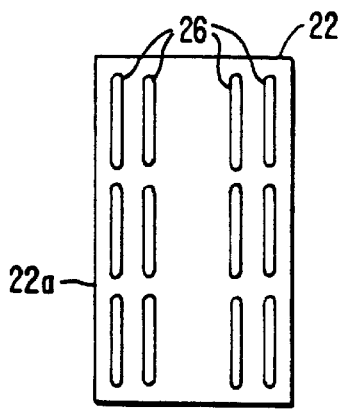
FIGS. 5D–G illustrate the structure and electrical layout of the electrode array for the probe of FIGS. 5A and B.
Figure 5E:
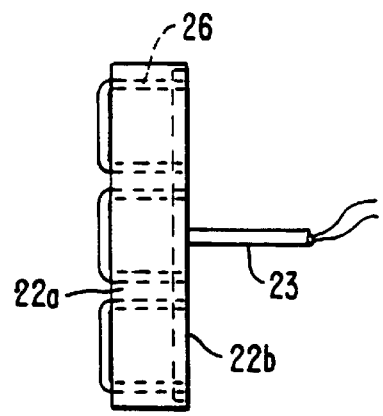

An exemplary structure for probe body 22 of probe 20' is illustrated in FIGS. 5D and E. Electrodes 26 are formed from wires of stainless steel, copper, or the like, but may alternatively comprise plates oriented perpendicularly to the treatment surface, the plates having rounded or radiused edges, with only the edges exposed. Electrodes 26 are coupled to the power supply with wires or other conductors disposed between a main probe body 22a and a back insulating layer 22b. The conductors extend proximally through hypotube 23, which may also include a lumen for delivering a conduction enhancing liquid or gel, typically for delivery of about 1 cc/min of saline through one or more weep holes in treatment surface 24 adjacent or between the pairs of electrodes (as can be understood with reference to FIG. 14). Probe body 22 will typically be rigid in this embodiment, often being formed of a polymer such as ABS plastic, polycarbonate, or the like, but may alternatively be semi-rigid (typically comprising silicone or nylon).

Probe 20 may optionally include a variety of mechanisms to actively control contraction of the target tissue. Optionally, body 22 may include multiplexing circuitry which selectively directs electrical energy supplied through a limited number of conductors to the electrodes or electrode pairs. Such circuitry will optionally vary the electrical energy or duty cycle of the electrodes depending on temperatures measured at or near the electrodes. Alternatively, a uniform heating energy may be directed from treatment surface 24 based on one or more temperature measurements, based on dosimetry, or the like. Circuitry for probe 20 may incorporate microprocessors or the like. Alternatively, signals may be transmitted from the probe to an external processor for control of the contraction energy.

Figure 5F:
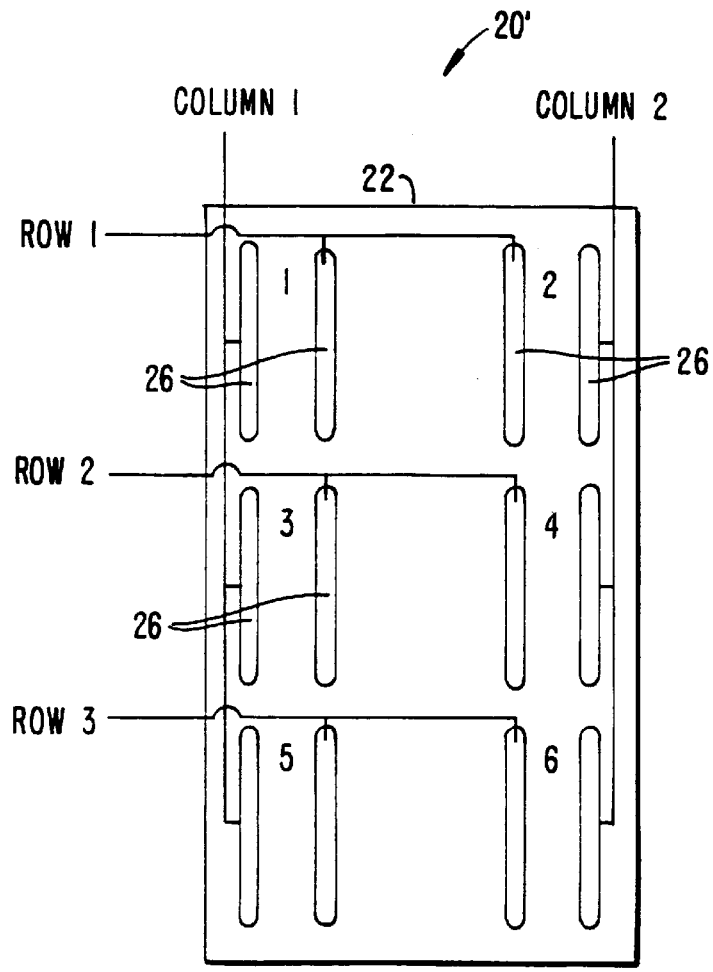

Exemplary probe circuits are illustrated in FIGS. 5F and G. The coupling arrangement illustrated in FIG. 5F allows an M×N array of electrode pairs to be selectably energized using only M+N conductors. This arrangement takes advantage of the fact that current (and heating) will be concentrated along the path of least electrical resistance, which will generally be between the two closest bipolar electrodes. In this case, rows of electrodes are coupled together and columns of electrodes are coupled together so that a particular electrode pair 1, 2, 3, . . . 6 is selected by driving a current between the associated column and the associated row. For example, electrode pair 3 is selected by driving bipolar current between the electrodes of column 1 and the electrodes of row 2. Current (and heating) between energized electrodes other than pair 3 will not be sufficient to significantly contract tissue. In the exemplary embodiment, the electrode pairs are energized by heating each pair associated with a column starting with the middle pair (for example, pair 3, then pair 1, then pair 5), and then moving on to the next column (for example, pair 4, pair 2, and then pair 6).

Figure 5G:
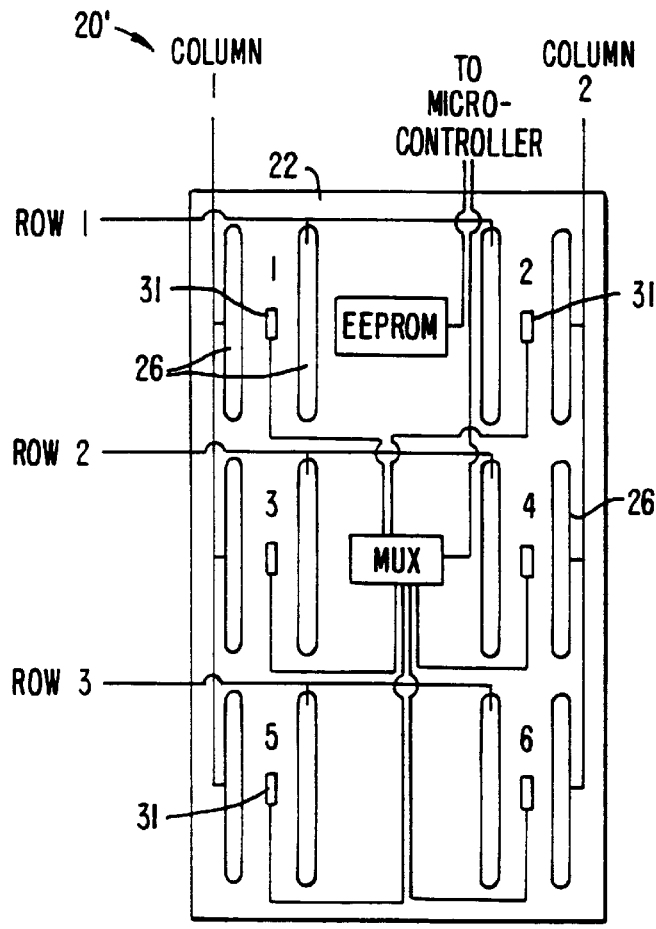

The probe circuit of FIG. 5G allows the electrode pairs to be selectively energized, and further provides calibrated temperature information from adjacent each electrode pair (temperatures may be monitored selectively, for example, at the active electrode only). Temperature sensors 31 may comprise thermistors, thermocouples, or the like, and will be mounted to probe body 22 so as to engage the tissue between a pair of electrodes to limit the number of signal wires, temperature sensors 31 are coupled to a multiplexer MUX mounted in handle 25, or possibly in probe body 22. As such temperature sensors provide temperature signals which are repeatable (for each mounted sensor) though not necessarily predictable, the accuracy of the temperature feedback can be enhanced by storing calibration data for this probe, and ideally for each temperature sensor, in a non-volatile memory such as an EEPROM.

Figure 6A:
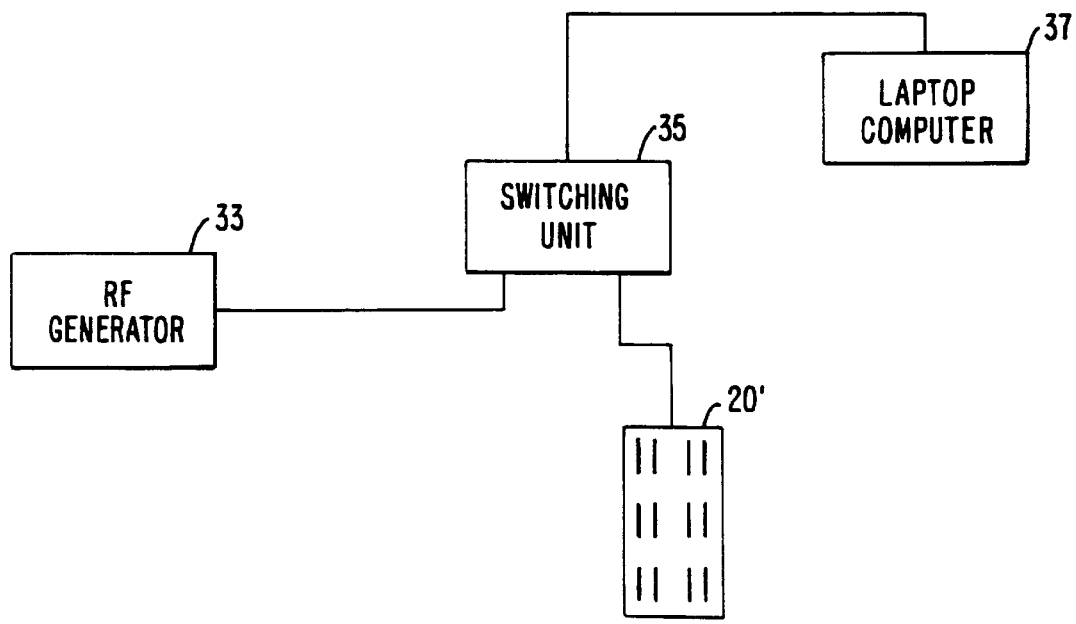
FIGS. 6A–C are schematic block diagram showings of a static tissue contraction system having an electrode array with optional temperature feedback signals.
Figure 6B:
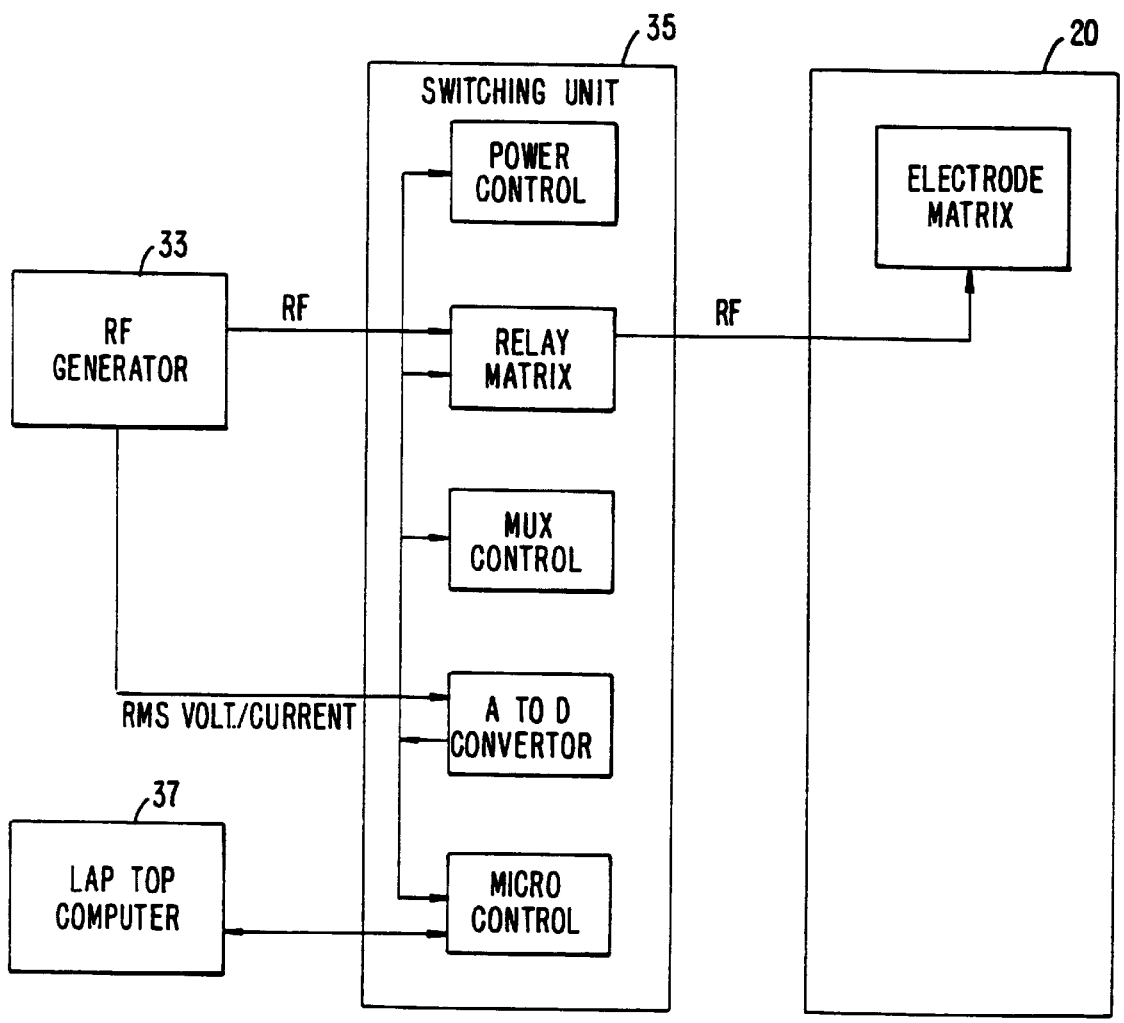
Figure 6C:
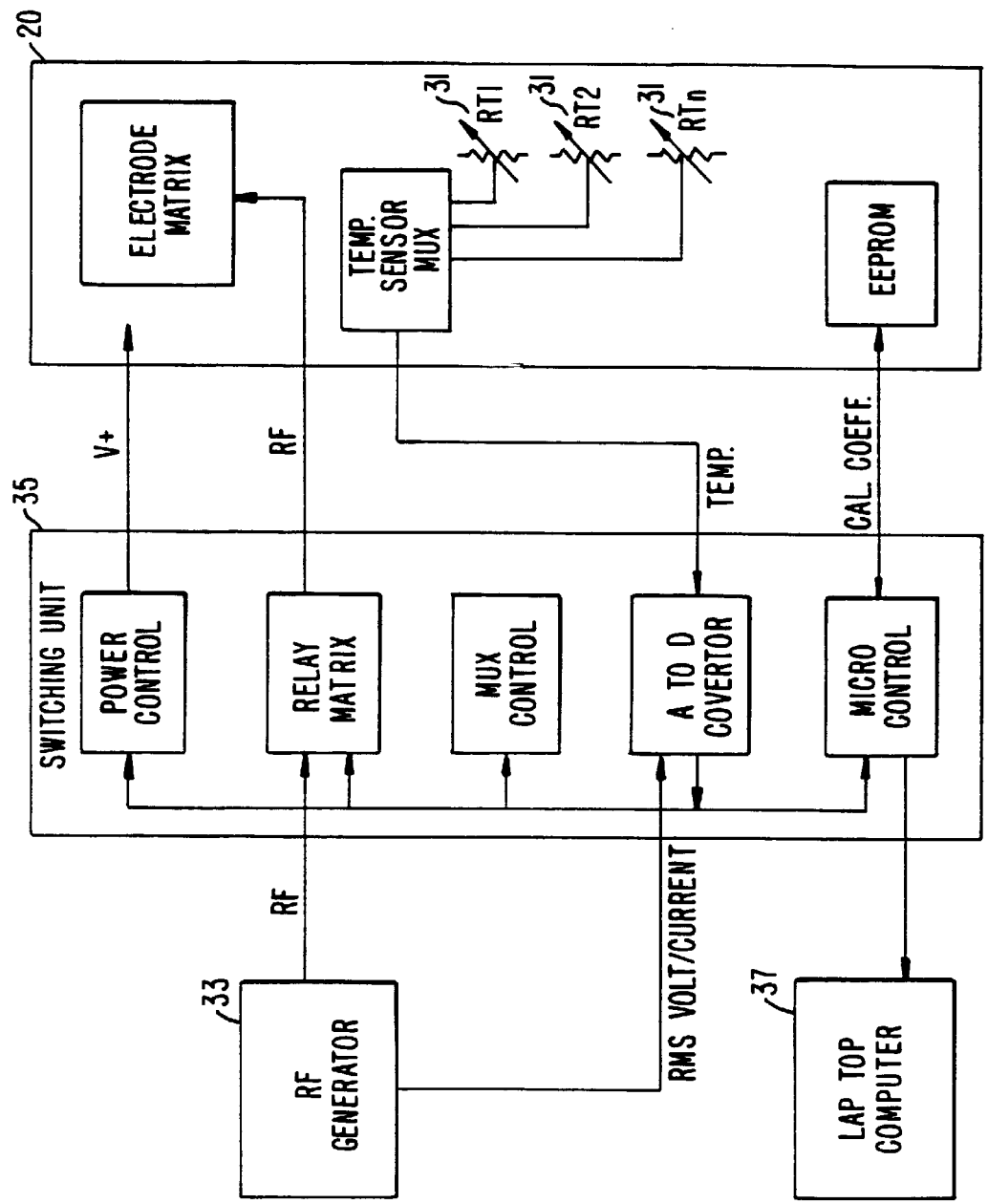

Static contraction systems including probe 20 are shown schematically in FIGS. 6A–C. In general, power from an electrical power source 33 is directed to the electrodes of probe 20' by a switching unit 35 under the direction of a processor 37. These functions may be combined in a variety of arrangements, such as by including the processor and the switching unit, some or all of the switching unit circuitry with the probe, or the like. Where temperature feedback is provided, such as in the system of FIG. 6C, the temperature may be controlled by selectively energizing and halting power to the probe (sometimes called a bang-bang feedback control) to maintain the desired temperature or temperature profile, or the controller and/or switching unit may selectively vary the power level.

Advantageously, the total desired shrinkage of a discrete target region of endopelvic fascia EF may be controlled without moving probe 20. Total contraction of the endopelvic fascia will depend on a number of factors. Generally, tissue will contract locally by up to 70% (areal shrinkage) when heated to contraction temperature range. Therefore, it is possible to select a probe 20 having a treatment surface 24 with a size and shape suitable for providing a total effective contraction of endopelvic fascia EF so as to provide the desired improvement in support of the pelvic floor. It may therefore be desirable to provide a series of differing probes for contracting tissues by differing amounts. For example, it may be possible to select a probe having a lateral dimension of 12 mm to decrease an effective lateral dimension of the right portion of the endopelvic fascia by 5 mm. A greater amount of contraction might be effected by selecting an alternate probe with a greater width. Selecting probes having differing lengths, selecting among alternative probes having treatment surfaces 24 which are wider at one end than the other, or selectively positioning the probe along the midline might allow the surgeon to tailor the enhanced support to lift the anterior or posterior portions of the bladder to a greater or lesser degree, as desired.

Still further alternative contraction control mechanisms might be used. Rather than selecting alternative probes, it may be possible to vary the heating energy among the electrodes. Where a lesser degree of contraction is desired, the surgeon may heat the tissue to a lower temperature, and/or may selectively heat only a portion of the tissue which engages treatment surface 24 (for example, by energizing only a selected subset of electrodes 26). Electrical properties of the system can be monitored before, during, between, and/or after energizing the probe with tissue heating current. For example, as the controller selectively energizes the electrode pairs, the system impedance can be monitored to help ensure that sufficient electrode/tissue coupling is maintained for the desired treatment. In a simple feedback indication arrangement, a warning light may illuminate to inform the surgeon that coupling was (or is) insufficient. More sophisticated feedback systems may re-treat selected undertreated areas by re-energizing electrode pairs for which coupling was compromised. Generally, these feedback systems generate a feedback signal FS to indicate an effect of the treatment on the tissue, as schematically illustrated in FIG. 6A. Feedback signal FS may simply provide an indication to the surgeon, or may be processed by the controller to modify the treatment. Regardless, this controlled contraction can be provided without moving probe 20.

Methods for accessing target regions of the endopelvic fascia are illustrated in FIGS. 7A–E. In general, endopelvic fascia EF can be viewed as left and right fascial portions separated at the patient's midline by urethra UR. Endopelvic fascia EF is supported by ligaments ATFP above a vaginal wall VW. It may be desirable to selectively shrink endopelvic fascia EF along target regions 40 which extend in an anterior posterior direction along the left and right sides of the endopelvic fascia. This should provide enhanced support of urethra UR, the bladder neck, and the bladder with little risk of heating, denervating or injuring the delicate urethral tissues.

Figure 7A:
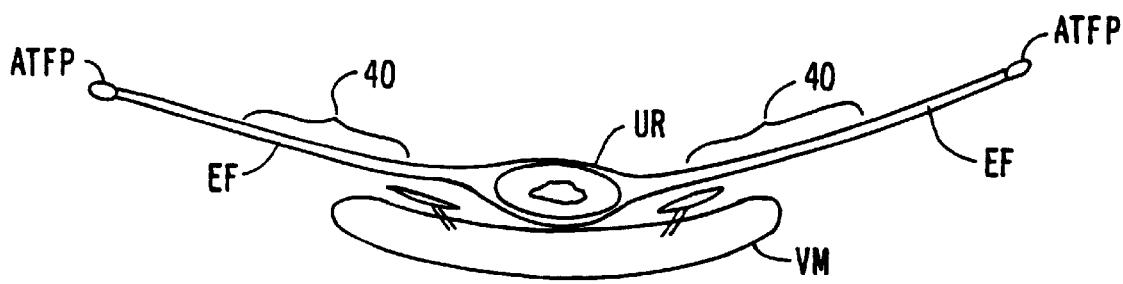
FIGS. 7A–E schematically illustrate methods for accessing left and right target regions of the endopelvic fascia.
Figure 7B:
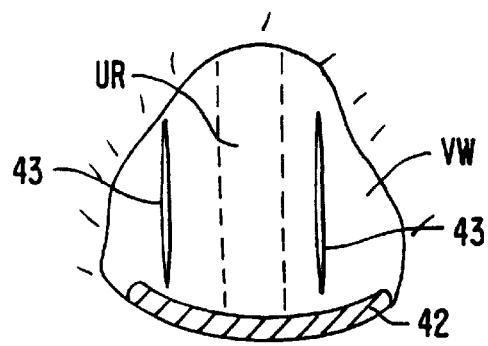
Figure 7C:
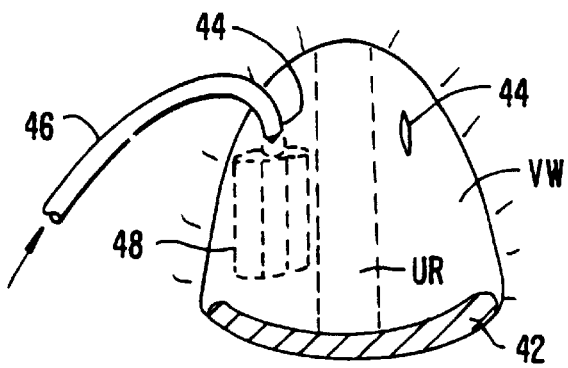
Figure 7D:
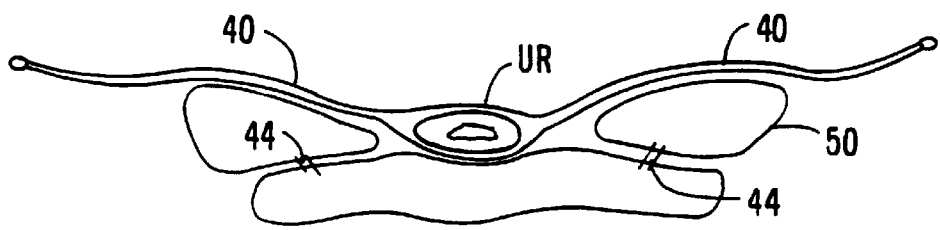

To access target regions 40 with minimal trauma to the patient, a weighted speculum 42 is inserted into the vagina to expose the anterior vaginal wall VW. Optionally, elongated laterally offset incisions 43 might be made in the anterior vaginal wall so that the vaginal mucosa could be manually dissected to reveal the endopelvic fascia EF. However, to minimize trauma and speed healing, a small incision 44 may be made on either side of urethra UR, thereby allowing access for a minimally invasive blunt dissection device 46. Dissection device 46 includes a mechanical expansion element in the form of a balloon 48 at its distal end. Balloon 48 dissects the back side of the vaginal wall from the endopelvic fascia to create a minimally invasive treatment site 50 along each of the discrete target regions 40, as seen in FIG. 7D. Regardless of the specific access technique, the exposed endopelvic fascia will preferably be irrigated with saline or the like to reduce fouling of the electrodes, and to enhance electrode/tissue coupling with a conductive film. The patient will preferably be positioned so that excess irrigation fluid drains from the tissue surface, and aspiration will often be provided to clear any drained fluids.

Figure 7E:
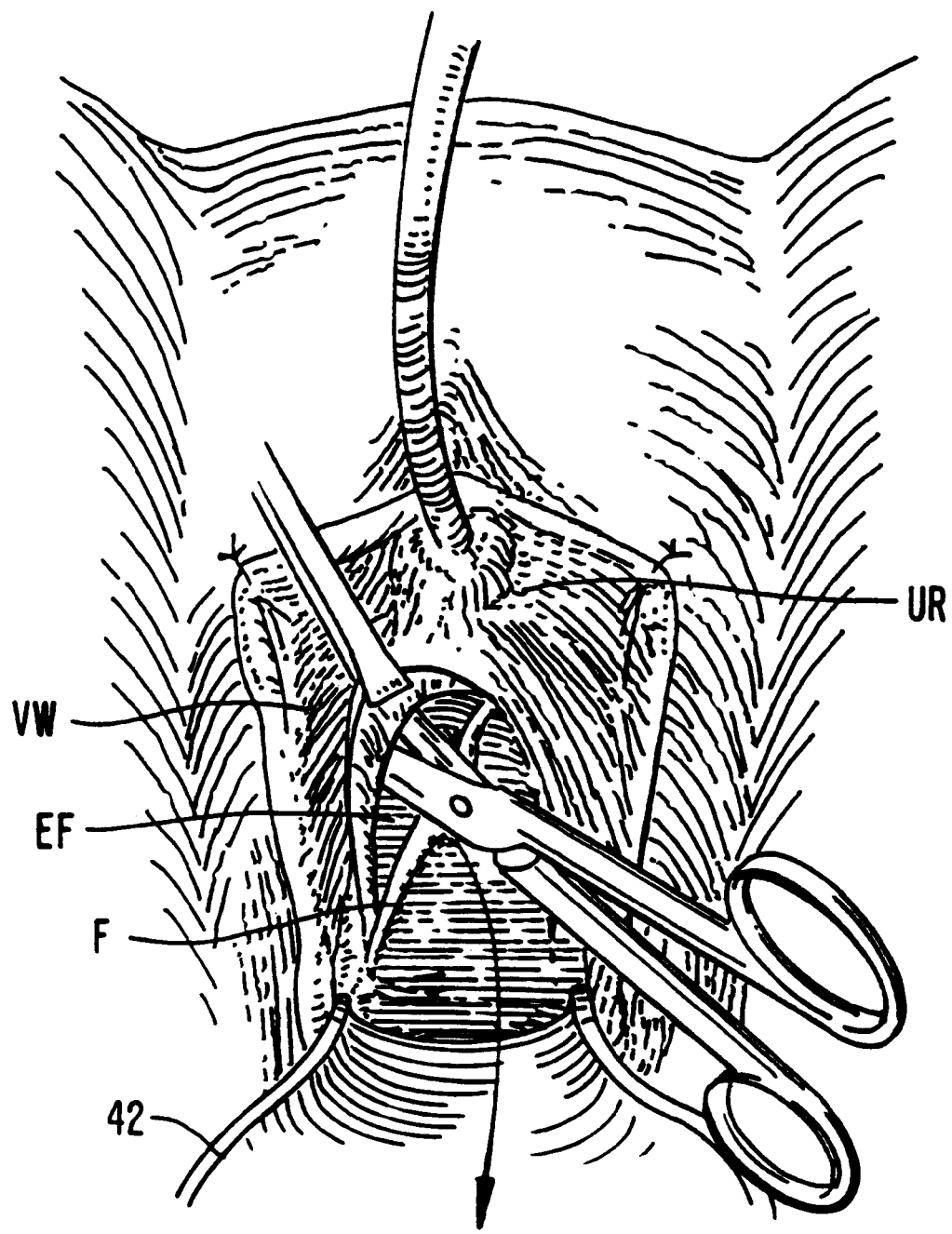

An alternative method for accessing the endopelvic fascia is illustrated in FIG. 7E. This is sometimes referred to as the Raz technique, and generally comprises separating an arch-shaped mid-line flap F from the surrounding vaginal wall VW to access the underlying and adjacent endopelvic fascia as shown. This procedure was described in more detail by Shlomo Raz in *Female Urology,* 2nd. Ed. (1996) on pages 395–397.

Figure 8:
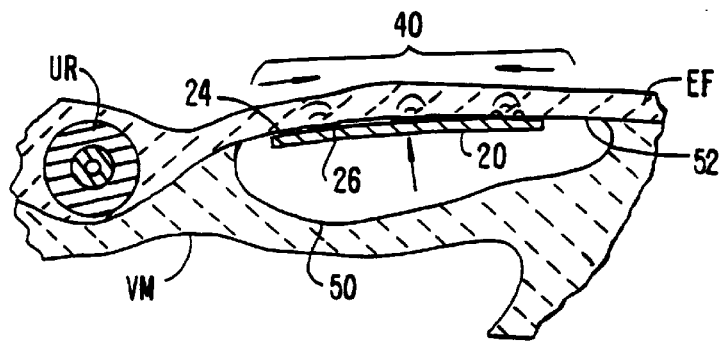
FIG. 8 is a cross-sectional view showing a method for treating a left target region of the endopelvic fascia.

Referring now to FIG. 8, probe 20 is inserted through incisions 43 or 44 to treatment site 50. Treatment surface 24 is urged against exposed surface 52 of endopelvic fascia EF so that electrodes 26 are effectively coupled with the endopelvic fascia. Probe 20 may be biased against the endopelvic fascia manually by pressing against the wall of vaginal mucosa VM, by pressing directly against the probe using a finger inserted through incision 43 or 44, or using a shaft attached to the probe that extends proximally through the incision. Alternatively, as will be described hereinbelow, probe 20 may include a mechanical expansion mechanism for urging treatment surface 24 against the endopelvic fascia EF.

Once the probe engages target region 40 of endopelvic fascia EF, electrodes 26 are energized via conductors 28 (see FIG. 5). Electrodes 26 direct electrical current through the endopelvic fascia so that the resistance of the fascia causes an increase in tissue temperature. The use of relatively large electrode surfaces having a sufficiently large radius of curvature avoids excessive concentration of electrical current density near the tissue/electrode interface which might cause charring, tissue ablation, or excessive injury to the tissue.

As endopelvic fascia EF is heated by probe 20, the collagenated tissues within the fascia contract, drawing the tissue inward along treatment surface 24. Although probe 20 does not move during this contraction, it should be noted that at least a portion of endopelvic fascia EF may slide along treatment surface 24, since the tissue contracts while the probe generally does not.

Figure 9A:
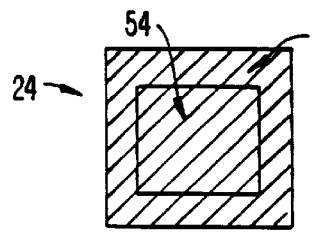
FIGS. 9A–D schematically illustrate a picture frame shaped tissue contraction device having an independently energizeable peripheral portion so as to treat tissue surrounding an initially contracted region.
Figure 9C:
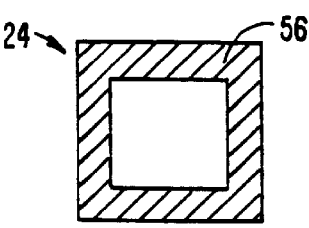
Figure 9B:
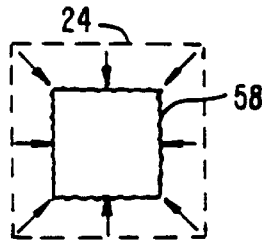
Figure 9D:
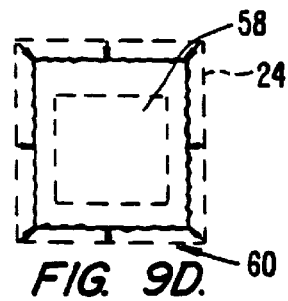

As can be understood with reference to FIGS. 9A–D, the probes of the present invention can effectively treat a larger region of the target tissue than is initially engaged by the treatment surface. FIG. 9A schematically illustrates a treatment surface 24 having a peripheral "picture frame" portion 56 which can be energized independently of an interior portion 54. By energizing both portions 54 and 56, tissue 58 engaging treatment surface 24 contracts inward as shown in FIG. 9B. Once this first stage of tissue has been contracted, however, additional heating of the contracted tissue will generally not provide contraction to the same degree, but may impose additional injury. Therefore, peripheral portion 56 can be energized independently of the interior portion so that the uncontracted tissue 60 that now engages treatment surface 24 can be safely contracted.

While interior portions 54 and peripheral portion 56 are illustrated as contiguous treatment zones, it should be understood that they may actually comprise independently energizeable arrays of electrodes. Additionally, it should be understood that peripheral portion 56 need not completely surround interior portion 54, particularly where the probe includes some structure that affixes a portion of the probe relative to the engaged tissue.

Figure 10A:
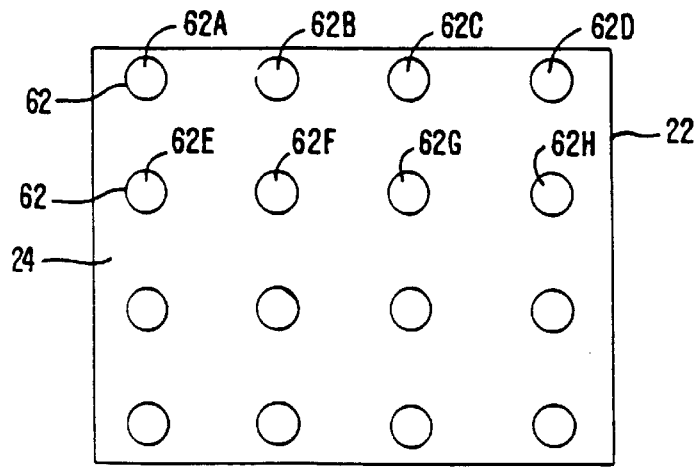
FIGS. 10A and B illustrate an alternative probe having a two-dimensional electrode array.
Figure 10B:

A wide variety of alternative electrode array structures might be used. As illustrated in FIG. 10A, electrodes 62 may optionally comprise monopolar or bipolar rounded buttons or flat disks defining a two-dimensional array. In some embodiments, a temperature sensor may be provided for each button. For bipolar heating, radiofrequency current may be driven from one button electrode to another. Alternatively, radiofrequency current may be driven from each button to a large surface area pad applied against the patient's back in a monopolar configuration.

When used in a bipolar mode, it may be desirable to drive radiofrequency current between pairs of electrodes that are separated by at least one other electrode. This may allow heating to a more even depth, as heating energy will be concentrated near the engaged tissue surface adjacent each electrode, but will be distributed to a greater depth midway between the electrodes of a bipolar pair. For example, it is possible to drive radiofrequency current from electrode 62a to electrode 62c, from electrode 62b to electrode 62d, from electrode 62e to electrode 62g, from electrode 62f to electrode 62h, and the like.

Advantageously, in an N×M electrode array, it is possible to independently drive each of these electrode pairs using only N+M conductors between the driving power source and the electrodes, as described above regarding FIG. 5F.

A wide variety of alternative electrode and probe structures may be used. For example, the button electrodes of FIGS. 10A and B may be mounted on an inflatable balloon which could be rolled up into a narrow configuration for insertion to the treatment site. The balloon could then be inflated to allow engagement of the treatment surface against the target tissue.

Figure 11A:
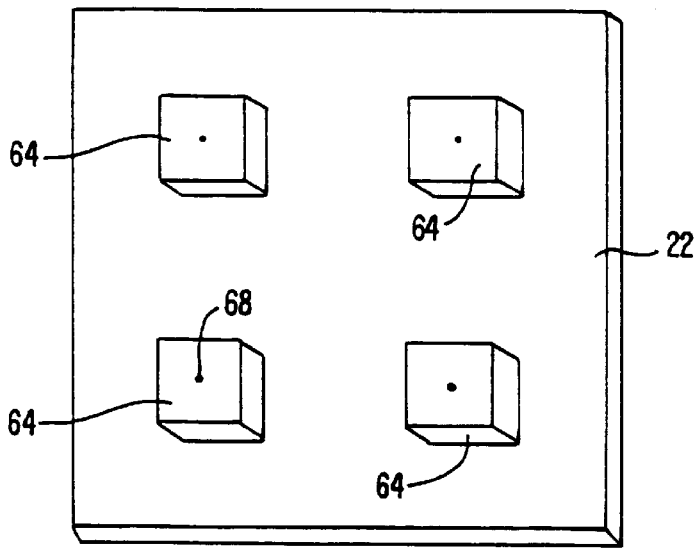
FIGS. 11A and B illustrate a probe structure having a two-dimensional array of posts for independently engaging, heating and contracting tissue, in which the posts may optionally include resistive heaters and temperature sensors.

A still further alternative probe structure is illustrated in FIGS. 11A and B. In this embodiment, a two-dimensional array of protrusions 64 each include a resistive heater 66 and a temperature sensor 68. As heat transfer between the probe and the tissue is by conduction of heat rather than by conduction of electrical current, the ends of protrusions 64 can safely include corners without concentrating heat. Hence, the protrusions can have heat transfer ends that are round, square, hexagonal, or the like, and the protrusions can be cylindrical, conical, or some other desired shape. Alternatively, flush heat transfer surfaces may be formed with similar structures.

Preferably, the protrusions 64 can be pressed against the tissue surface and resistive heaters 66 can be energized while active temperature feedback is provided by temperature sensor 68. This feedback can be used to heat the protrusions to the desired treatment temperature for a predetermined time so as to effect the desired tissue contraction. Alternatively, the temperature sensors may measure the actual temperature of the tissue, rather than that of the protrusion.

Figure 12:
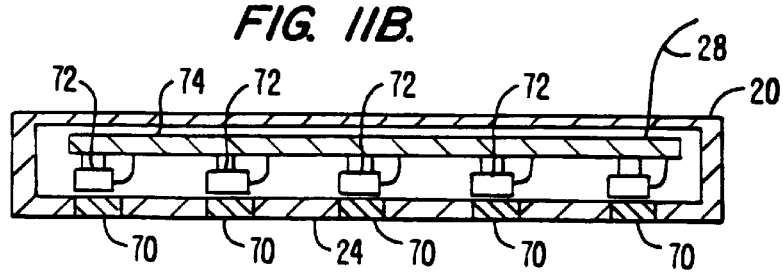
FIG. 12 is a cross-sectional view of a probe structure having heat transfer surfaces thermally coupled to diodes and to the target tissue so as to allow the diodes to act as both heaters and temperature sensors.

Referring now to FIG. 12, a two-dimensional array of heat transfer surfaces 70 might make use of thermally conductive materials that extend from or are flush with treatment surface 24. At least one electrical component 72 is thermally coupled to an associated heat transfer surface 70 so that the component varies in temperature with the temperature of the surface. The component will typically have an electrical characteristic which varies with temperature, the component typically comprising a transistor, thermistor, or silicon diode. Component 72 can be coupled to conductor 28 using a printed circuit board 74.

Electrical current is driven through component 72 so that the component heats heat transfer surface 70. The tissue engaging heat transfer surface 24 is heated by passive conduction from heat transfer surfaces 70. Preferably, the heating electrical current is applied as intermittent pulses. Between heating pulses, a small constant current can be driven through a diode in a forward direction, and the voltage across the junction can be measured using printed circuit board 74. The forward voltage across this junction is often dependent on the temperature of the junction, typically varying by about 2 mV/° C. for a silicon diode. This forward voltage can be used to measure the junction temperature. The timing of the heating pulses and the structure of heat transfer surface 70 can be set so that the diode junction will indicate the temperature of the tissue against which the heat transfer surface is engaged, with the diode junction preferably being at or near an equilibrium temperature during a slow gradual heat cycle.

The temperature indication signal provided by the low-power, between heating pulse can be used as a feedback control signal. The array ideally comprises a two-dimensional array, and feedback signals from multiple heat transfer surfaces of the array should allow very good control of the local tissue contraction temperature throughout the treatment surface/tissue interface. Such an array of transistors or diodes coupled to a power source via conductor 28 and printed circuit board 74 provides a very inexpensive way to selectively control the temperature across treatment surface 24.

Figure 12A:
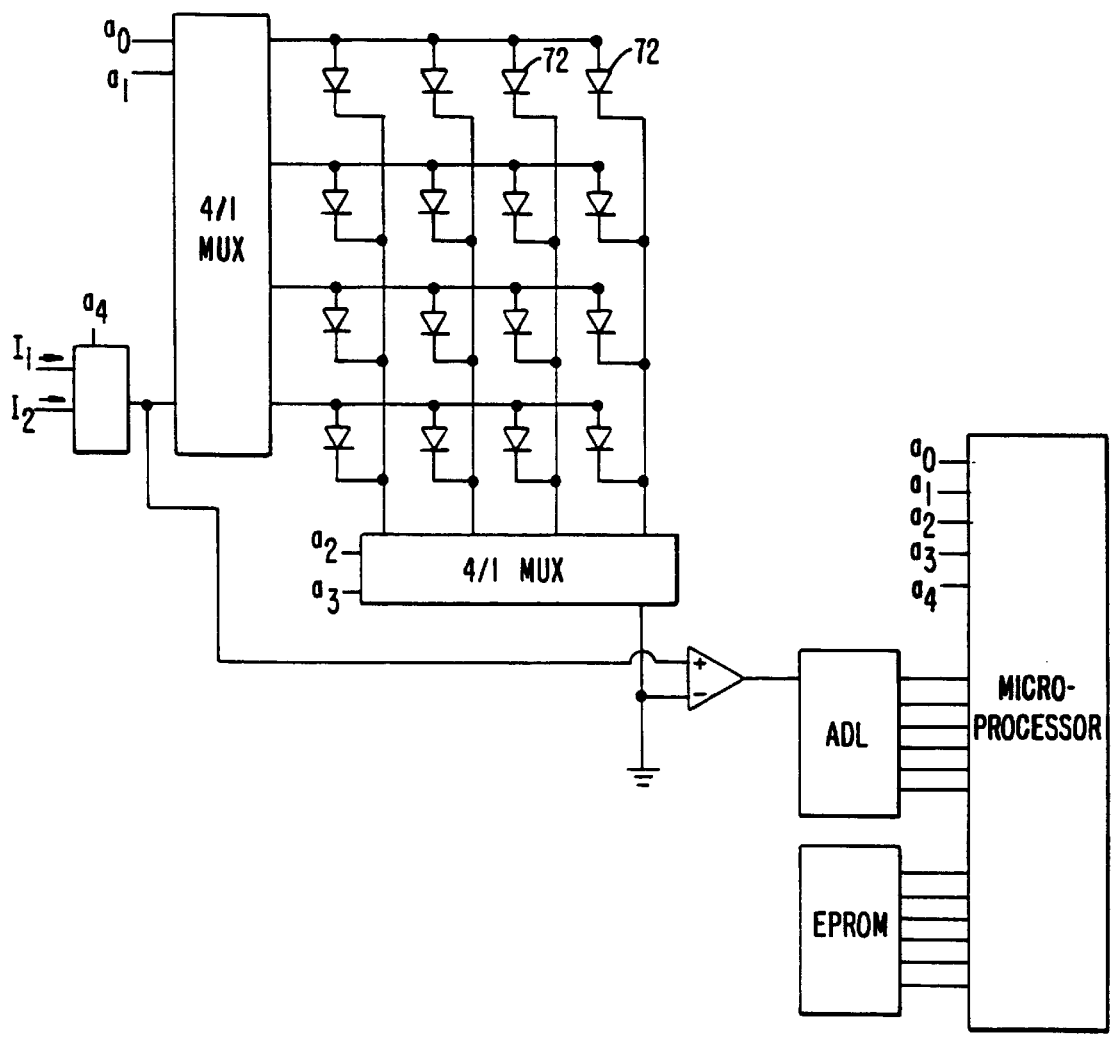
FIG. 12A is a drive/feedback block diagram for the probe of FIG. 12.

FIG. 12A is an exemplary circuit including the probe of FIG. 12. A large variable current $I_1$ is sufficient to heat diodes 72 so as to treat the engaged tissue, preferably under proportional control. A small constant current $I_2$ does not significantly heat the engaged tissue, but does allow measurement of the forward voltage drop across each diode. Applying a constant small current $I_2$, the voltage drop across a diode 72 thermally coupled (through a metal plate) to the tissue will be about 0.7 v–2 mV/° C. for a silicon diode so as to indicate the tissue temperature. Once again an EEPROM or other non-volatile memory may store calibration data for each diode, ideally storing calibration constants for at least two temperatures from calibration tests conducted prior to delivery and/or use of the probe.

Figure 13:
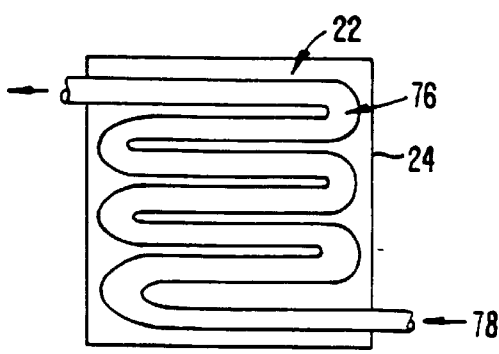
FIG. 13 illustrates an alternative probe structure in which a conduit directs a heated fluid along a treatment surface of the probe.
Figure 14:
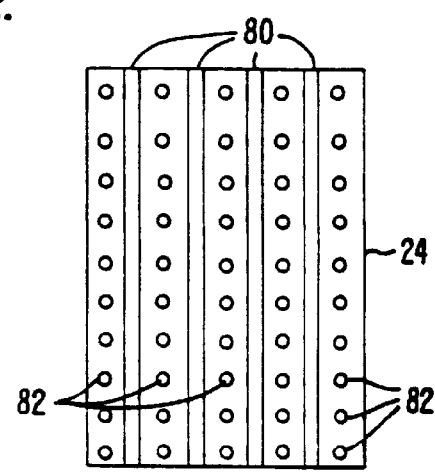
FIG. 14 illustrates a still further alternative probe in which a plurality of irrigation ports are disposed between a one-dimensional array of elongate electrodes.

As illustrated in FIGS. 13 and 14, still further alternative heating mechanisms might be used. In FIG. 13, a conduit 76 directs a relatively high temperature fluid along a serpentine path adjacent treatment surface 74, the heated fluid typically comprising steam or the like. In the embodiment of FIG. 14, a one dimensional array of elongate electrodes 80 is distributed across treatment surface 24, with irrigation ports 82 being disposed between and/or around the electrodes.

When accessing the endopelvic fascia transvaginally, the midline need not be dissected, as described above. This minimizes the possibility of inadvertently treating and/or injuring the urethra. Generally, treatment can be made symmetric by statically positioning the probe against the target region on the left side of the endopelvic fascia, and statically positioning the same or a different probe on the right side of the endopelvic fascia without accessing the fascia adjacent the urethra. Alternatively, it may be possible to treat only one side and effectively inhibit incontinence, particularly where only one side of the endopelvic fascia has an excessive length. Nonetheless, it may be desirable to access the endopelvic fascia across the midline, particularly when treating both the left and right target regions simultaneously with a single probe.

The use of a semi-rigid probe body 22 can be understood with reference to FIG. 15. Probe 20 flexes when held against endopelvic fascia EF by a force F to ensure engagement between treatment surface 24 and the endopelvic fascia throughout the desired interface region. Optionally, probe body 22 may be pre-curved to facilitate coupling between the treatment surface and the target tissue. For example, a thin flat probe body which is slightly convex might be held against the target tissue by pressure F2 at the edges of the treatment surface (rather than a central pressure F) until the device becomes substantially flat, thereby indicating to the surgeon that the proper amount of tissue engaging pressure is being applied.

FIG. 16 illustrates a structure and method for aligning probe body 22 along the endopelvic fascia so that treatment region 40 is separated from the urethra by a protection zone 86. A catheter 88 is introduced into the urethra, which facilitates identification of the urethra along the endopelvic fascia. Optionally, cooled water may be circulated through the catheter to avoid any injury to the urethra during treatment. It should be understood that such a urethral cooling system may be desirable for many embodiments of the present systems and methods.

To facilitate aligning treatment surface 24 with target region 40, urethra UR is received in a cavity 88 of probe body 22. Cavity 88 is separated from treatment surface 24 by a desired protection zone 86. As a method for using this probe will generally involve dissecting the mucosa from the endopelvic fascia so as to access the fascia near urethra UR, the probe body may extend bilaterally on both sides of the urethra to simultaneously treat the left and right portions of the endopelvic fascia, as is indicated by the dashed outline 90. Such a bilateral system can avoid injury to the urethral tissues by heating two (left and right) discrete treatment regions separated by a protection zone. Bilateral systems might evenly treat the two sides of the endopelvic fascia by sequentially energizing two separated arrays of electrodes in a mirror-image sequence, the two sides being treated simultaneously, sequentially, or in an alternating arrangement.

Referring now to FIGS. 17A–C, the static tissue contraction probes of the present invention may optionally include an expansion mechanism such as balloon 92 to urge treatment surface 24 against the target tissue. The device might again be inserted through incisions into the anterior vaginal wall on either side of the urethra. Electrodes 26 are again mounted on a probe body 22 which is at least semi-rigid, with a resilient balloon 92 molded to the back of the probe body. The balloon can be inflated after the probe is positioned to urge treatment surface 24 against the target tissue with a repeatable electrode/fascia interface pressure.

Balloon 92 will preferably comprise an elastomer such as silicone or the like.

To improve coupling between the electrodes and the target tissue, defibrillator gel or saline may be provided at the treatment surface/tissue interface. These enhanced coupling materials may be placed on the probe or tissue surface prior to engagement therebetween, or may alternatively be delivered through ports adjacent the electrodes.

Figure 18A:
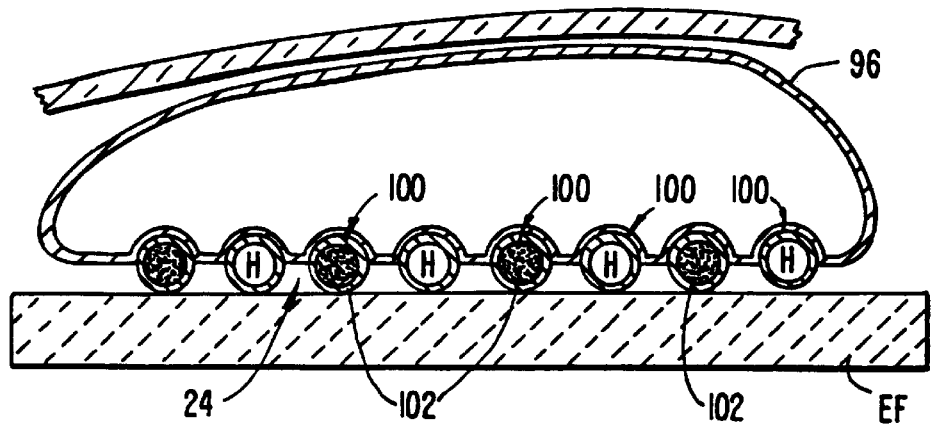
FIGS. 18A–C illustrate a minimally invasive probe having interspersed heating and cooling areas to effect tissue contraction with minimal damage to the target tissue, and in which the probe includes a balloon that can be inserted to a treatment site in a narrow configuration and expanded at the treatment site to engage and treat the full target region without moving the probe.
Figure 18B:
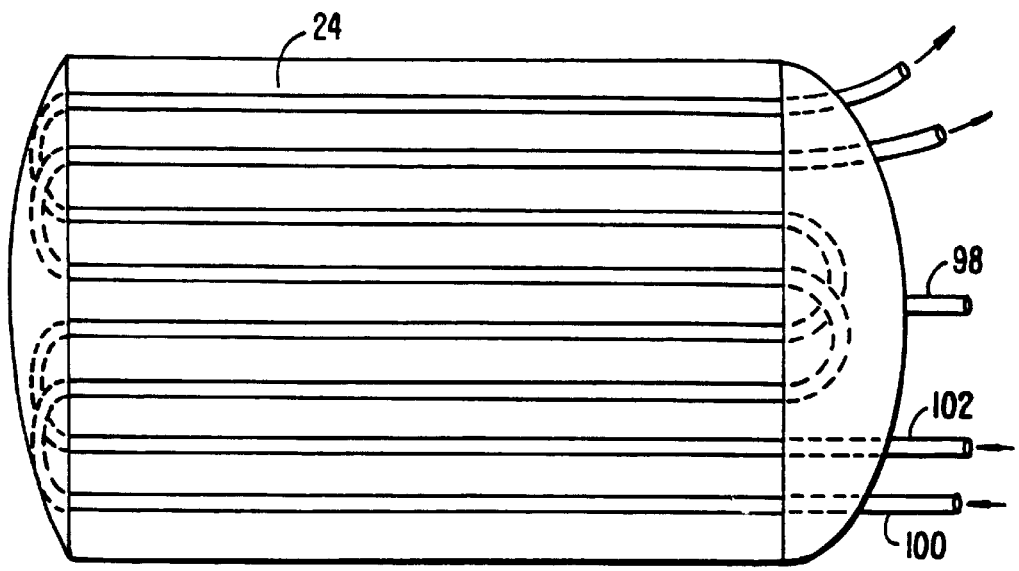
Figure 18C:
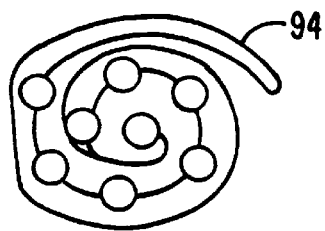

FIGS. 18A–C illustrate a still further alternative probe structure. In this embodiment, an expandable probe 94 is inserted through a small incision while the probe is in a narrow configuration. Once the probe is positioned adjacent the target tissue, balloon 96 is inflated via an inflation lumen 98. The balloon expands against an opposing tissue so as to urge treatment surface 24 against the endopelvic fascia.

Once inflated, fluid is passed through conduits adjacent the treatment surface to thermally treat the endopelvic fascia. In this embodiment, a hot fluid conduit 100 is arranged in a serpentine pattern which alternates with a cold fluid conduit 102 so that the treatment surface comprises interspersed zones of heating and cooling. Heating tissues to a safe contraction temperature between cooled zones will induce contraction with less injury to the tissue than would otherwise be imposed, as the regions of heated tissue are interspersed with, and protected by, the tissue cooling.

Still further alternative treatment mechanisms are illustrated in FIGS. 19A–C, and in FIG. 20. In the embodiment of FIGS. 19, tissue heating and cooling are interspersed using a device which includes a heated plate 104 having a series of 30 heated protrusions 106 in combination with a cooled plate 108 having interspersed cooled protrusions 110 and passages 112. Passages 112 receive heated protrusions 106, while a thermally insulating material 114 insulates the plates surrounding the protrusions from each other and the target tissue.

This device may optionally make use of active resistive heating of the entire hot plate 104, in some cases with temperature feedback provided from a single temperature sensor. In such cases, hot plate 104 will preferably be thick enough so that heat transfer through the plate from protrusion to protrusion is sufficient so that the temperature gradient from one protrusion to another is negligible, allowing uniform treatment across the treatment surface. In alternative embodiments, protrusions 106 may not be actively heated while in contact with the target tissue. Instead, hot plate 104 may be heated prior to contact with the tissue so that heat transfer to the tissue is provided by the heat capacity of hot plate 104, as predetermined from the specific heat of the hot plate material, the quantity of hot plate material, and the like. In fact, the device may be preheated in an oven or the like, so that no active heating of the plate is provided for. Instead, the plate has sufficient heat capacity to treat the tissue if applied to the tissue for a predetermined amount of time.

Figure 11B:
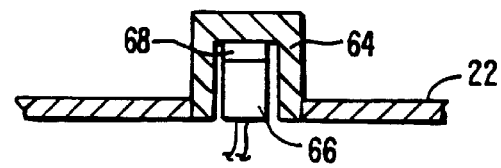

In some embodiments, protrusions 106 may include resistive heating elements such as those described above regarding FIGS. 11A–12, optionally using a combination of resistive heating and the heat capacity of the protrusions and/or plate. Likewise, cold plate 108 may include a chilled fluid conduit, thermoelectric cooling module, or the like for actively cooling the plate, and/or may make use of the heat capacity of the plate to passively cool the tissue through cooled protrusions 110.

FIG. 20 illustrates an energy transmission element which is self-limiting. In this embodiment, a heat transfer surface 116 (typically defined by a metal barrier) is heated by boiling an aqueous gel 118. Gel 118 is boiled by a resistive heater 120, and the steam is directed through a nozzle 122 in an insulating material 124. The heated steam heats the heat transfer surface 116. Once the gel has boiled away, insulating material 124 substantially blocks the heat from resistive heater 120 from reaching the heat transfer surface 116. Advantageously, this provides a maximum temperature determined by the boiling point of the aqueous gel, without requiring a temperature sensor. Furthermore, the maximum amount of heat delivered to the tissue is determined by the initial mass of the aqueous gel provided.

Figure 21:
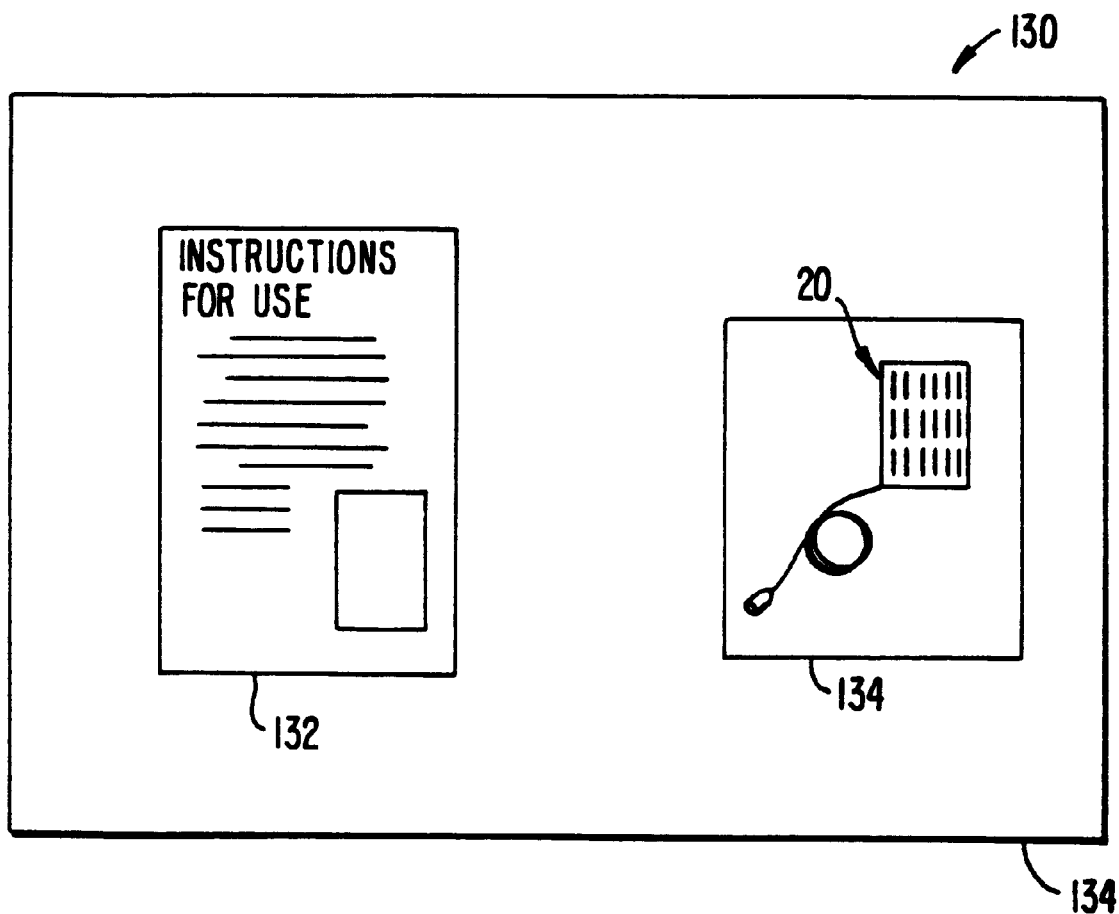
FIG. 21 illustrates a tissue contracting kit including the probe of FIG. 5 and instructions for its use.

FIG. 21 schematically illustrates a kit 130 including probe 20 and its instructions for use 132. Probe 20 may be replaced by any of the probe structure described herein, while instructions for use 132 will generally recite the steps for performing one or more of the above methods. The instructions will often be printed, optionally being at least in-part, comprise a video tape, a CD-ROM or other machine readable code, a graphical representation, or the like showing the above methods.

While the exemplary embodiments have been described in some detail, by way of example and for clarity of understanding, a variety of modifications, changes, and adaptations will be obvious to those of skill in the art. Therefore, the scope of the present invention is limited solely by the appended claims.

What is claimed is:

1. In a therapy for inhibiting incontinence by effecting a desired contraction of a discrete target region within an endopelvic support tissue, a method comprising: engaging a surface of a probe against the discrete target region of the endopelvic support tissue; and directing energy from an array of transmission elements disposed on the probe surface into the support tissue, without moving the probe, so as to effect the desired contraction of the target region, by transmitting the energy across a probe surface/tissue interface having a length of at least 10 mm and a width of at least 5 mm, the energy being sufficient to contract the endopelvic support tissue without ablating the endopelvic support tissue.

2. The method of claim 1, further comprising engaging a curving surface of the probe against an endopelvic fascia, the curving surface being at least semi-rigid.

3. The method of claim 2, further comprising flexing the curving surface of the probe against the target region so that each element of the array is electrically coupled with the endopelvic fascia, the elements comprising electrodes.

4. The method of claim 3, wherein the flexing is effected by pushing manually against a thin flat probe body.

5. The method of claim 1, further comprising engaging a semi-rigid or rigid probe surface against an endopelvic fascia.

6. In a therapy for inhibiting incontinence by effecting a desired contraction of a discrete target region within an endopelvic support tissue, a method comprising:

engaging a surface of a probe against the discrete target region of the endopelvic support tissue; and directing energy from a two-dimensional array of electrodes disposed on the probe surface into the support tissue, without moving the probe, so as to effect the desired contraction of the target region, by applying bipolar electrical energy between pairs of the electrodes, wherein at least one electrode of the array is disposed between at least one of the pairs.

7. In a therapy for inhibiting incontinence by effecting a desired contraction of a discrete target region within an endopelvic support tissue, a method comprising:

engaging a surface of a probe against the discrete target region of the endopelvic support tissue;

directing energy from an array of transmission elements disposed on the probe surface into the support tissue, without moving the probe so as to effect the desired contraction of the target region; and controlling the energy so that the support tissue is heated to a temperature in a range from about 70° C. to about 140° C. and varying a distribution of electrical power to the elements of the array.

8. In a therapy for inhibiting incontinence by effecting a desired contraction of a target region of an endopelvic support tissue, a method comprising:

engaging a surface of a probe against a tissue surface to provide a probe/tissue interface with a length of at least 10 mm and a width of at least 5 mm;

directing energy from an array of electrodes through the probe/tissue interface into the support tissue, without moving the probe, so as to effect the desired contraction of the target region; and controlling the energy by applying bipolar electrical energy between pairs of the electrodes and by alternating the energized electrodes so that the bipolar energy overlaps.

9. In a therapy for inhibiting incontinence by effecting a desired contraction of a discrete target region within an endopelvic support tissue, a method comprising:

engaging a surface of a probe against the discrete target region of the endopelvic support tissue;

directing energy from a two-dimensional array of electrodes along the probe surface into the support tissue, without moving the probe, so as to effect the desired contraction of the target region; and controlling the energy so that the support tissue is heated to a temperature in a range from about 70° C. to about 140° C. for a time in a range from about 0.5 to about 40 seconds.

* * * * *